United States Patent
Tsuji et al.

(10) Patent No.: US 6,900,360 B2
(45) Date of Patent: May 31, 2005

(54) HIGH-PURITY 1,3-BUTYLEN GLYCOL, PROCESS FOR PRODUCING 1,3-BUTYLENE GLYCOL, AND PROCESS FOR PRODUCING BY-PRODUCT BUTANOL AND BUTYL ACETATE

(75) Inventors: Yasuo Tsuji, Ohtake (JP); Hiroaki Uenakai, Kakogawa (JP); Hiroshi Koyama, Hidaka (JP)

(73) Assignee: Daicel Chemical Industries, Ltd., Sakai (JP)

( * ) Notice: Subject to any disclaimer, the term of this patent is extended or adjusted under 35 U.S.C. 154(b) by 215 days.

(21) Appl. No.: 09/958,129

(22) PCT Filed: Feb. 2, 2001

(86) PCT No.: PCT/JP01/00771

§ 371 (c)(1),
(2), (4) Date: Jan. 2, 2002

(87) PCT Pub. No.: WO01/56963

PCT Pub. Date: Aug. 9, 2001

(65) Prior Publication Data

US 2003/0018224 A1 Jan. 23, 2003

(30) Foreign Application Priority Data

| Feb. 4, 2000 | (JP) | ........................ | 2000-027026 |
|---|---|---|---|
| Feb. 4, 2000 | (JP) | ........................ | 2000-027028 |
| Feb. 4, 2000 | (JP) | ........................ | 2000-027031 |
| Feb. 4, 2000 | (JP) | ........................ | 2000-027033 |
| Feb. 4, 2000 | (JP) | ........................ | 2000-027037 |
| Feb. 4, 2000 | (JP) | ........................ | 2000-027039 |

(51) Int. Cl.[7] .................... C07C 31/18; C07C 31/20
(52) U.S. Cl. ............... 568/852; 568/862; 568/863; 568/864; 568/868
(58) Field of Search ................... 568/852, 862, 568/863, 864, 868

(56) References Cited

U.S. PATENT DOCUMENTS

| 3,489,655 A | 1/1970 | Peveto et al. |
|---|---|---|
| 5,345,004 A | 9/1994 | Nishiguchi |
| 6,028,215 A | 2/2000 | Bessling et al. |
| 6,376,725 B1 | 4/2002 | Tsuji et al. |

FOREIGN PATENT DOCUMENTS

| EP | 1046628 | 10/2000 |
|---|---|---|
| GB | 853266 | 11/1960 |
| JP | B1-39-001658 | 2/1964 |
| JP | B-69014328 | 6/1969 |
| JP | B-70-010483 | 4/1970 |
| JP | A-61065834 | 4/1986 |
| JP | 62-212384 | 9/1987 |
| JP | A-62-246529 | 10/1987 |
| JP | A-63-156738 | 6/1988 |
| JP | 07258129 | 10/1988 |
| JP | 63-29664 | 11/1994 |
| JP | A-09-225311 | 9/1997 |

OTHER PUBLICATIONS

International Search Report—International Application No. PCT/JP01/00771.

*Primary Examiner*—Elvis O. Price
(74) *Attorney, Agent, or Firm*—Morgan & Finnegan, LLP

(57) ABSTRACT

A method is provided for the preparation of high-purity 1,3-butylene glycol from acetaldehyde. In the method, acetaldehyde is condensed in the presence of base to form a mixture of acetaldols, and the acetaldols are then converted to 1,3-butylene glycol by hydrogenation. Chemical treatment and distillation processes are described which provide 1,3-butylene glycol of very high purity.

28 Claims, 1 Drawing Sheet

HIGH-PURITY 1,3-BUTYLEN GLYCOL, PROCESS FOR PRODUCING 1,3-BUTYLENE GLYCOL, AND PROCESS FOR PRODUCING BY-PRODUCT BUTANOL AND BUTYL ACETATE

TECHNICAL FIELD

In the present invention, a first invention group relates to 1,3-butylene glycol of high purity, which, at a period of three months after production, exhibits potassium permanganate color-fading time of at least five minutes as measured according to JIS K1351 3.10, and which issues no odor and undergoes minimal change in quality with passage of time. A second invention group relates to a process for producing purified a 1,3-butylene glycol, characterized by hydrogenating acetaldols in the presence of a catalyst for hydrogenation having a specific activity. The purified 1,3-butylene glycol issues a slight odor or no odor. A third invention group relates to a process for producing 1,3-butylene glycol by hydrogenating, in the presence of a catalyst, acetaldols under acidic conditions. A fourth invention group relates to a process for purifying 1,3-butylene glycol, in which a crude reaction mixture obtained through hydrogenation of acetaldols in the presence of a catalyst is basified, and alcohols are removed from the mixture. Further, a fifth invention group relates to a process for producing a purified 1,3-butylene glycol, characterized by subjecting 1,3-butylene glycol to an ozone treatment after high-boiling-point components are removed in the form of residue in tower bottom. The purified 1,3-butylene glycol issues a significantly reduced odor, and is suitable as, for example, a raw material for cosmetics. Still further, a sixth invention group relates to a process for producing butanol as a by-product (in the present invention, the butanol refers to n-butanol) by hydrogenating crotonaldehyde which is by-produced during synthesis of acetaldols; and to a process for producing butyl acetate from the butanol.

BACKGROUND ART 1,3-Butylene glycol is a viscous, colorless, transparent, odorless liquid having a boiling point of 208° C., exhibits high solubility, and produces derivatives having excellent chemical stability.

1,3-Butylene glycol is used as a raw material of various synthetic resins and surfactants. In addition, since 1,3-butylene glycol has excellent hygroscopicity, low volatility, and low toxicity, it is also used as a material for cosmetics, hygroscopic agents, high-boiling-point solvents, and antifreezes. Particularly, in recent years, there has been increasing a demand for a non-toxic, non-irritant 1,3-butylene glycol in the cosmetic industry, since the butylene glycol has excellent properties as a humectant. Thus, an odorless butylene glycol is useful as a material of cosmetic grade.

However, when stored in a tank, 1,3-butylene glycol produced through a conventional process deteriorates with passage of time and issues a slight odor, and thus, long-term storage of the butylene glycol has been difficult.

Therefore, there has been a demand for providing an odorless 1,3-butylene glycol and which does not issue even a slight odor after storage for a long period of time.

Conventionally, the following three production processes for 1,3-butylene glycol have been known: (I) a process for producing 1,3-butylene glycol in which acetaldehyde is subjected to aldol condensation to thereby yield acetaldols, followed by catalytic reduction of the acetaldols (UK Patent No. 853266); (II) a process for producing 1,3-butylene glycol through a hydration reaction of 1,3-butylene oxide; and (III) a process for producing 1,3-butylene glycol from propylene and formaldehyde through the Prins reaction.

However, the process (II) is not practical, since an industrial production process therefor has not yet been established. Also, the process (III) is not practical because of a low yield.

Industrially, 1,3-butylene glycol is produced through the process (I). However, since acetaldols are a structurally unstable substance, and produces crotonaldehyde through dehydration, a variety of impurities such as butanol and 2-butanone are by-produced during a hydrogenation step (hereinafter, abbreviated as hydrogenation). Furthermore, in a step for recovering and recycling acetaldehyde, acetaldols are reacted with, for example, acetaldehyde, to thereby produce a variety of impurities. Separation of such impurities is difficult during a step for purifying 1,3-butylene glycol through, for example, distillation, and the impurities adversely affect the quality, particularly odor, of a product, for example, a product for cosmetics in particular.

Japanese Patent Application Laid-Open (kokai) No. 62-212384 discloses a process for producing substantially paraldol (trivial name of 2-(2-hydroxypropyl)-4-methyl-1,3-dioxane-6-ol), in which acetaldehyde is subjected to aldol condensation in the presence of an alkali catalyst, to thereby yield a crude reaction mixture containing aldoxane (trivial name of 2,4-dimethyl-1,3-dioxane-6-ol), and the aldoxane is thermally decomposed while acetaldehyde is obtained as a distillate.

Japanese Patent Application Laid-Open (kokai) No. 62-246529 discloses a process for producing 1,3-butylene glycol, in which a starting material containing paraldol as a substantially effective component is subjected to catalytic reduction.

Japanese Patent Publication (kokoku) No. 44-14328 discloses a process for producing crotonaldehyde, in which acetaldehyde is subjected to aldol condensation in the presence of an alkali catalyst, to thereby synthesize aldol, and dehydration of the aldol is carried out under heating in the presence of an acidic phosphoric acid ester.

Japanese Patent Application Laid-Open (kokai) No. 61-65834 discloses a process for purifying 1,3-butylene glycol, in which 1,3-butylene glycol having a purity of 98% or more is continuously distilled and purified under reduced pressure by use of a thin-film evaporator, while water is added to the butylene glycol.

Japanese Patent Application Laid-Open (kokai) No. 63-156738 discloses a process for distilling and purifying 1,3-butylene glycol, in which a hydrogenation reaction mixture of acetaldol is promptly subjected to flash evaporation under reduced pressure in advance, and the hydrogenation reaction mixture is subjected to distillation for removing high-boiling-point substances, and then to distillation for removing low-boiling-point substances, to thereby produce 1,3-butylene glycol as a bottom product.

Japanese Patent Application Laid-Open (kokai) No. 6-329664 discloses a process for producing a crude reaction mixture predominantly containing aldoxane and paraldol, in which, when acetaldehyde is subjected to aldol condensation in the presence of an alkali catalyst to thereby produce a crude reaction mixture predominantly containing aldoxane, acetaldehyde, water, and a small amount of crotonaldehyde, and then the aldoxane is thermally decomposed to thereby produce a crude reaction mixture predominantly containing the aldoxane and paraldol, acetaldehyde obtained as a distillate from the top of a thermal decomposition tower during thermal decomposition of the aldoxane is purified by use of a distillation tower including a side cut line having a decanter, and acetaldehyde substantially not containing crotonaldehyde is recycled in the aldol condensation step; and a process for producing 1,3-butylene glycol from the crude reaction mixture.

Japanese Patent Application Laid-Open (kokai) No. 7-258129 discloses a process for distilling and purifying 1,3-butylene glycol from a reaction mixture obtained through liquid-phase hydrogen reduction of acetaldol, in which, when 1,3-butylene glycol is subjected to distillation for removing high-boiling-point substances, at least one compound selected from the group consisting of sodium hydroxide, potassium hydroxide, sodium borohydride, and potassium borohydride is added to the reaction mixture.

U.S. Pat. No. 3,489,655 discloses a process for improving the odor of 1,3-butylene glycol through a specific distillation process, in which heated 1,3-butylene glycol is brought into contact with only a non-catalytic material; specifically, stainless steel or glass.

However, the thus-produced odorless 1,3-butylene glycol involves a problem in that the butylene glycol deteriorates with passage of time and issues a slight odor when stored for a long period of time. Since a solution fed into a tower for removing high-boiling-point substances contains large amounts of high-boiling-point substances, through addition of an alkali metal, although the amount of low-boiling-point substances which are responsible for odor is reduced, simultaneously the high-boiling-point substances are decomposed to thereby yield low-boiling-point substances. It is to be noted that substances causing odor can be consequently reduced but only to a certain limited amount, and thus the butylene glycol deteriorates as time elapses, to thereby issue a slight odor when stored for a long period of time.

As described above, the conventional techniques are unsatisfactory for producing, at high yield and low cost, 1,3-butylene glycol which issues a considerably reduced odor after being stored for a long period of time, or 1,3-butylene glycol of high purity.

Meanwhile, butyl acetate is widely used as, for example, a solvent. Known production processes for butyl acetate include a process for distilling and purifying butyl acetate obtained through esterification of acetic acid and butanol in the presence of an acid catalyst.

Known production processes for butanol serving as a raw material include (i) the Hoechst-Wacker process, in which acetaldol is synthesized through dimerization of acetaldehyde and subjected to dehydration, to thereby yield crotonaldehyde, and then the crotonaldehyde is hydrogenated (hereinafter, occasionally also referred to hydrogenation); and (ii) the Reppe process, in which propylene, carbon monoxide, and water are reacted with one another in the presence of a catalyst.

On the other hand, when acetaldols are synthesized through condensation of acetaldehyde, and the acetaldols are hydrogenated, to thereby produce 1,3-butylene glycol, crotonaldehyde is by-produced during the synthesis step of the acetaldols. Therefore, there has been studied a process for producing butyl acetate from butanol which is by-produced through hydrogenation of the by-produced crotonaldehyde.

However, through the aforementioned techniques, production of butanol, or butyl acetate, having a quality comparable with that of a commercially available product is difficult, since the chameleon test value or the sulfuric acid coloring test value of butanol is low due to impurities contained in by-produced butanol.

Accordingly, the first invention group provides 1,3-butylene glycol of high purity which, at a period of three months after production, issues a considerably reduced odor, and which undergoes minimal change in quality with passage of time. The second invention group provides a process for producing, reliably and at high production efficiency, 1,3-butylene glycol which does not issue any problematic odor immediately after production and after three months of storage. The third invention group provides a process for producing 1,3-butylene glycol at high yield, in which corrosion of an apparatus employed in a hydrogenation step is minimized. The fourth invention group provides a high-yield, economical purification process for providing 1,3-butylene glycol of high purity. Further, the fifth invention group provides a high-yield, economical process for producing purified 1,3-butylene glycol which issues no odor or issues only a considerably reduced odor.

Furthermore, the sixth invention group provides a process for producing, as a by-product, butanol containing small amounts of impurities, in which, when acetaldol is hydrogenated to thereby produce 1,3-butylene glycol, crotonaldehyde which is by-produced during synthesis of the acetaldols is simultaneously hydrogenated, to thereby allow butanol to be by-produced, and the by-produced butanol is purified; and a process for producing butyl acetate of high quality from the thus-obtained butanol.

DISCLOSURE OF THE INVENTION

In order to solve the aforementioned problems, the present inventors have performed extensive studies, and have found that, when 1,3-butylene glycol is produced such that the 1,3-butylene glycol exhibits potassium permanganate color-fading time of at least five minutes as measured according to JIS K1351 3.10, the odor of the 1,3-butylene glycol is considerably reduced, and the 1,3-butylene glycol undergoes a minimal change in quality with passage of time, to thereby accomplish the inventions belonging to the first invention group.

The present inventors have found that, when acetaldols are hydrogenated in the presence of a catalyst of high activity, the amount of the aldehyde groups remaining in the resultant crude mixture (referred to as "hydrogenation crude mixture")—the aldehyde groups being considered to be a substance responsible for odor—can be considerably reduced, to thereby accomplish the inventions belonging to the second invention group.

The present inventors have found that, when acetaldols obtained through condensation of acetaldehyde in the presence of a basic catalyst are hydrogenated in the presence of a hydrogenation catalyst and under acidic conditions, the aforementioned problems can be solved, to thereby accomplish the inventions belonging to the third invention group.

The present inventors have found that, when a crude mixture obtained through hydrogenation of acetaldols (the mixture may be referred to as "hydrogenation crude mixture")—the mixture containing aldehyde—is basified and subjected to distillation, the aforementioned problems can be solved, to thereby accomplish the inventions belonging to the fourth invention group.

Further, the present inventors have found that, when a crude mixture obtained through hydrogenation of acetaldols (the mixture may be referred to as "hydrogenation crude mixture")—the mixture containing aldehyde—is subjected to distillation to thereby separate low-boiling-point components (L), the resultant mixture is further subjected to distillation to thereby yield 1,3-butylene glycol as a distillate, and then the 1,3-butylene glycol distillate (D) is treated with ozone, there can be produced a purified 1,3-butylene glycol which issues a considerably reduced odor or no odor (the glycol may be referred to as "a final product") at high yield and economically, to thereby accomplish the inventions belonging to the fifth invention group.

Still further, the present inventors have performed studies on the basis of the presumption that, in a process for producing butanol as a by-product, when by-produced crotonaldehyde is hydrogenated during production of 1,3-butylene glycol through hydrogenation of acetaldols, hydrogenation of the crotonaldehyde does not proceed completely, and reducing substances remain in a hydrogenation crude mixture, whereby the product quality of butanol, as a result, butyl acetate is lowered, since such impurities cannot be separated in a conventional distillation step for purifying the by-produced butanol, and a small amount of the impurities are contained in a purified butanol As a result, the present inventors have found that, when purification and a chemical treatment of by-produced butanol are carried out in combination, the butanol is effectively purified, to thereby accomplish the inventions belonging to the sixth invention group.

Accordingly, the first invention group provides a 1,3-butylene glycol which, at a period of three months after production, exhibits potassium permanganate color-fading time of at least five minutes as measured according to JIS K1351 3.10. There is also provided a 1,3-butylene glycol according to the first invention group, wherein the 1,3-butylene glycol is produced through hydrogenation of acetaldols in the presence of a catalyst.

The second invention group provides a process for producing a purified 1,3-butylene glycol, which comprises hydrogenating, in the presence of a catalyst, acetaldols obtained through condensation of acetaldehyde, to thereby yield a hydrogenation crude mixture containing 1,3-butylene glycol, wherein the catalyst is a Raney nickel having an acetone hydrogenation activity of 2,000 ml/g-Ni/hr or more and/or a phenol hydrogenation activity of 500 ml/g-Ni/hr or more. According to the second invention group, there is also provided a process for producing purified 1,3-butylene glycol wherein the amount of the aldehyde groups remaining in the hydrogenation crude mixture is 200 ppm by weight or less. According to the second invention group, there is also provided a process for producing purified 1,3-butylene glycol wherein the hydrogenation crude mixture is subjected to distillation to thereby separate low-boiling-point components (L), and then the mixture is further subjected to distillation to thereby yield 1,3-butylene glycol as a distillate. According to the second invention group, there is also provided a process for producing a purified 1,3-butylene glycol wherein the hydrogenation crude mixture is subjected to an evaporation treatment after the low-boiling-point components (L) are separated, and then the mixture is further subjected to distillation to thereby yield 1,3-butylene glycol as a distillate. According to the second invention group, there is also provided a process for producing a purified 1,3-butylene glycol wherein the hydrogenation crude mixture is subjected to distillation to thereby yield 1,3-butylene glycol as a distillate, and the 1,3-butylene glycol is subjected to distillation to thereby separate low-boiling-point components (1). According to the second invention group, there is also provided a process for producing a purified 1,3-butylene glycol wherein the odor of 1,3-butylene glycol as evaluated immediately after production has a rating of 3 or less. According to the second invention group, there is also provided a process for producing a purified 1,3-butylene glycol wherein the odor of 1,3-butylene glycol as evaluated after storage for three months has a rating of 5 or less.

The third invention group provides a process for producing 1,3-butylene glycol, which comprises hydrogenating, in the presence of a hydrogenation catalyst under an acidic condition, acetaldols obtained through condensation, in the presence of a basic catalyst, of acetaldehyde. According to the third invention group, there is also provided a process for producing 1,3-butylene glycol wherein the acidic condition is represented by an acidity (an amount (ml) of a 1/10 N sodium hydroxide aqueous solution to be required for neutralizing 100 ml of a sample) of 1–30. According to the third invention group, there is also provided a process for producing 1,3-butylene glycol wherein the acidic condition is attained by use of acetic acid.

The fourth invention group provides a process for purifying 1,3-butylene glycol, which comprises hydrogenating, in the presence of a catalyst, acetaldols obtained through condensation of acetaldehyde, to thereby synthesize 1,3-butylene glycol; and subjecting the 1,3-butylene glycol to distillation, wherein a hydrogenation crude mixture is basified, alcohols are removed from the mixture, followed by distillation. According to the fourth invention group, there is also provided a process for producing a purified 1,3-butylene glycol wherein alcohol is removed from the hydrogenation crude mixture, and the mixture is subjected to evaporation treatment, followed by distillation. According to the fourth invention group, there is also provided a process for purifying 1,3-butylene glycol wherein the basified hydrogenation crude mixture has a pH of 9–12. According to the fourth invention group, there is also provided a process for purifying 1,3-butylene glycol wherein the hydrogenation crude mixture is basified by use of sodium hydroxide or potassium hydroxide. According to the fourth invention group, there is also provided a process for purifying 1,3-butylene glycol wherein the hydrogenation crude mixture is basified after hydrogenation is carried out under a neutral or acidic condition.

The fifth invention group provides a process for producing a purified 1,3-butylene glycol, which comprises hydrogenating, in the presence of a catalyst, acetaldols obtained through condensation of acetaldehyde, to thereby synthesize 1,3-butylene glycol; and subjecting the 1,3-butylene glycol to distillation, wherein, after a hydrogenation crude mixture is subjected to distillation to thereby separate low-boiling-point components (L), 1,3-butylene glycol is distilled from the mixture, and the 1,3-butylene glycol distillate (D) is treated with ozone. According to the fifth invention group, there is also provided a process for producing a purified 1,3-butylene glycol wherein, after the hydrogenation crude mixture is subjected to distillation to thereby separate the low-boiling-point components (L), the mixture is promptly subjected to evaporation treatment, followed by distillation to thereby obtain the 1,3-butylene glycol distillate (D). There is also provided a process for producing a purified 1,3-butylene glycol according to the fifth invention group, wherein an ozone treatment is carried out by bringing 1 kg of the 1,3-butylene glycol distillate (D) into contact with 0.001–1 g of ozone. There is also provided a process for producing a purified 1,3-butylene glycol according to the fifth invention group, wherein low-boiling-point components (1) is separated from the ozone-treated 1,3-butylene glycol.

The sixth invention group provides a process for producing butanol, which comprises, when acetaldols are synthesized from acetaldehyde and the acetaldols are hydrogenated in a hydrogenation step to thereby produce 1,3-butylene glycol, hydrogenating crotonaldehyde which is by-produced during synthesis of the acetaldols during the hydrogenation step to thereby allow butanol to be by-produced; subjecting the produced 1,3-butylene glycol to distillation, to thereby separate a distillate (A) containing butanol; subjecting the distillate (A) to distillation, to thereby obtain a bottom solution (C) from which low-boiling-point components (B) are removed; subjecting the bottom solution (C) to a chemical treatment; and subjecting the resultant bottom solution (C) to distillation, to thereby separate low-boiling-point components (b) and high-boiling-point components (c) There is also provided a process for producing butanol according to the sixth invention group, wherein the chemical treatment is a sodium hydroxide treatment, a sodium borohydride treatment, an ozone treatment, or a combination of two or more of these treatments. There is also provided a process for producing butyl acetate, which comprises reacting butanol of the aforementioned invention with acetic acids.

Figure 1:
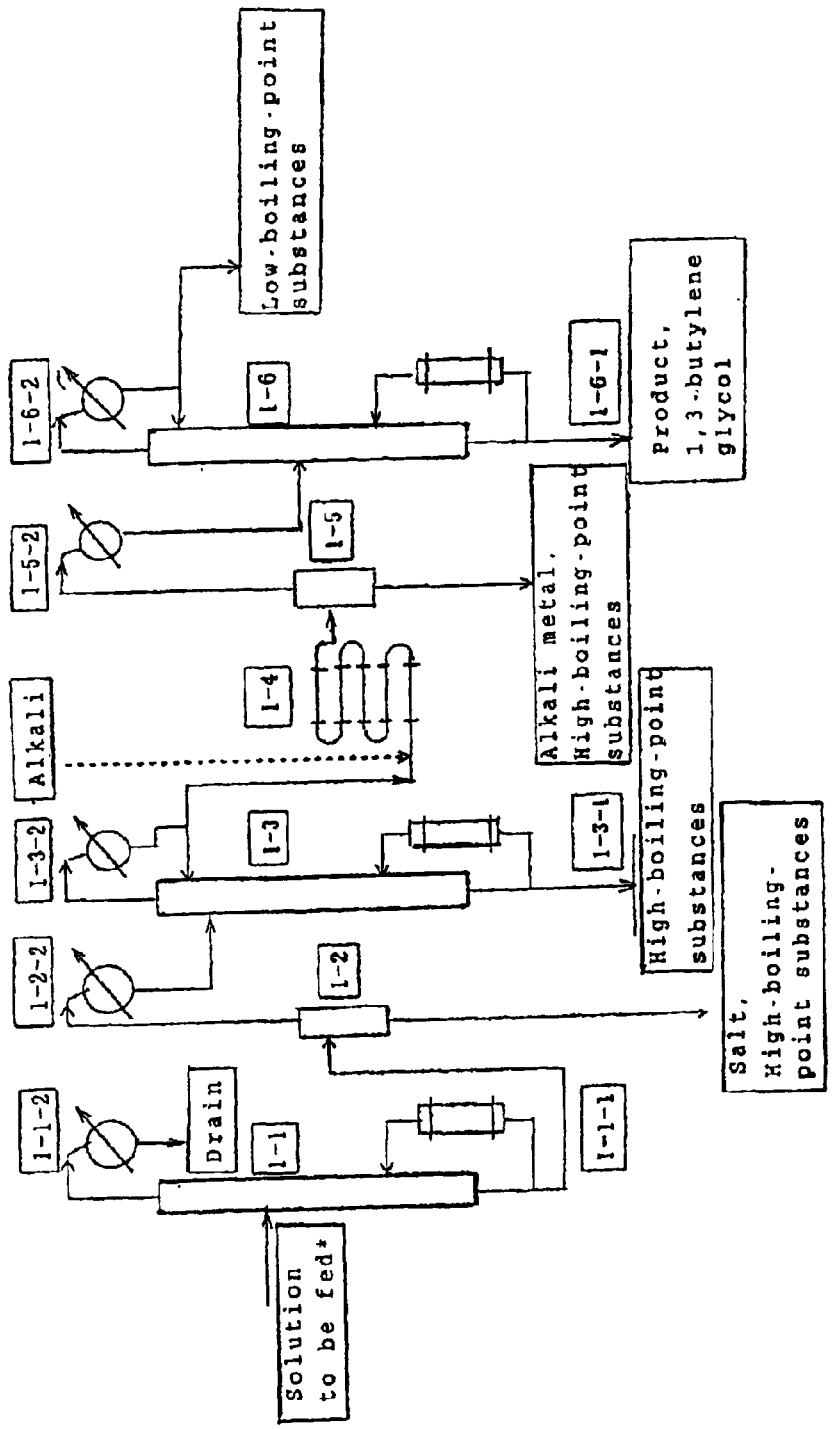
FIG. 1 is a flowsheet showing the purification process for 1,3-butylene glycol of the first invention group. An alkali metal compound is fed through a portion represented by a broken line.

The following are descriptions of reference numerals.

1-1; Dehydration tower

1-2: Salt-removal tower

1-3: Distillation tower for removal of high-boiling-point substances

1-4: Alkali reactor

1-5: Alkali-removal tower

1-6: Final product distillation tower

1-1-1, 1-3-1, 1-6-1: Reboiler

1-1-2, 1-2-2, 1-3-2, 1-5-2, 1-6-2: Condenser

BEST MODE FOR CARRYING OUT THE INVENTION

Embodiments of the first through sixth invention groups will next be described in detail. The following descriptions are common to the invention groups.

Acetaldols

Acetaldehyde, when condensed in the presence of a base such as sodium hydroxide, produces predominant component acetaldols, and further produces, upon dehydration of acetaldols, crotonaldehyde and other impurities as by-products. Acetaldols refer to a class of compounds which produce 1,3-butylene glycol through hydrogenation. Specific Examples of the acetaldols include acetaldol; paraldol which is a cyclic dimer thereof; aldoxane which is a cyclic trimer of acetaldehyde; and a mixture thereof.

Acetaldol or paraldol employed may be obtained directly through aldol condensation of acetaldehyde in the presence of a basic catalyst. There can be employed a mixture of paraldol and aldoxane which is obtained by thermally decomposing at least a portion of aldoxane into paraldol and acetaldehyde. During thermal decomposition, a small amount of crotonaldehyde may be by-produced.

Acetaldol, paraldol, aldoxane, or a mixture thereof may be used as a raw material for hydrogenation (hydrogenation reaction). A mixture (the mixture may be referred to as "crude reaction mixture") produced through condensation of acetaldehyde is usually neutralized with an acid in a neutralization step, and the mixture is used as a raw material for hydrogenation.

Characteristic features of the first invention group will next be described.

At least a portion of unreacted acetaldehyde is removed from a raw material for hydrogenation (hydrogenation reaction), since the unreacted acetaldehyde is usually recycled in a condensation step. However, the raw material for hydrogenation contains residual acetaldehyde, crotonaldehyde, small amounts of other aldehyde components, low-boiling-point substances, high-boiling-point substances such as aldehyde dimers and aldehyde trimers, and water. A raw material for hydrogenation containing water in an amount of 10–20% by weight can be used. A hydrogenation raw material having a purity of 95–98% by weight based on acetaldol components, exclusive of water, is preferably used.

Step Preceding Hydrogenation

Before hydrogenation, a raw material for hydrogenation may be optionally subjected to a preliminary treatment such as distillation for removing alcohols, dehydration distillation, removal of salts, or removal of impurities, and the thus-treated raw material from which unreacted acetaldehyde and by-products such as crotonaldehyde have been removed may be used.

Examples of the preliminary treatment include distillation, adsorption, ion exchange, heating for forming high-boiling-point substances, and decomposition. Examples of the distillation method employed include reduced-pressure distillation, ambient-pressure distillation, compressed distillation, azeotropic distillation, extracting distillation, and reactive distillation.

Hydrogen

The hydrogen to be employed for the hydrogenation is not particularly limited, and may be hydrogen which is usually used for hydrogenation in chemical synthesis. For example, the hydrogen has a purity of 99% by weight or more, preferably 99.5% by weight or more.

Catalyst

The catalyst to be used for the hydrogenation (the catalyst may be referred to as "hydrogenation catalyst") is not particularly limited, and, for example, a Raney nickel can be used.

Hydrogenation Step

The hydrogenation can be carried out through any of a batch-type process, a semi-batch-type process, and a continuous process.

The catalyst may be suspended in a raw material for hydrogenation or packed in a tower. Preferably, a catalyst is suspended in the raw material.

For example, a catalyst (2–20 parts by weight, preferably 5–10 parts by weight) is added to a raw material for hydrogenation (100 parts by weight), and the catalyst is suspended in the material with mixing or stirring under a hydrogen pressure of 80–200 kg/cm$^2$, preferably 120–150 kg/cm$^2$, at a temperature of 110–140° C., preferably 120–135° C., for 40–100 minutes, preferably 70–90 minutes, to thereby allow reaction to proceed.

However, 1,3-butylene glycol produced through hydrogenation of acetaldols is prone to contain minor amounts of low-boiling-point compounds having an unsaturated bond, such as acetaldehyde, butyraldehyde, crotonaldehyde, acetone, or methyl vinyl ketone, all of which are considered to be substances causing odor. Conventionally, it has been difficult to completely remove such the low-boiling-point compounds from 1,3-butylene glycol through distillation by use of a final product distillation tower. The term "the substance causing odor" refers to a substance which itself is a source of odor or a substance which with passage of time becomes an odoriferous substance.

Conventional 1,3-butylene glycol produced through hydrogenation of acetaldols, distillation, and purification does not exhibit sufficiently long potassium permanganate color-fading time as measured according to JIS K1351 3.10 immediately after production. Particularly, the color-fading time of conventional 1,3-butylene glycol after three months of storage is short, for example, 3 minutes or less, and thus, the glycol is considered to contain a substance which issues no odor immediately after production but which with passage of time undergoes change into an odoriferous substance.

A conventional purification process for 1,3-butylene glycol produced through hydrogenation of acetaldols is described below. After alcohols, water, salts, a catalyst, and high-boiling-point substances have been removed from a hydrogenation crude mixture containing 1,3-butylene glycol produced through catalytic reduction of acetaldols, the 1,3-butylene glycol was obtained, as a bottom product, from the bottom portion of a distillation tower (a final product distillation tower) for removing low-boiling-point substances.

An embodiment of production of 1,3-butylene glycol of high purity is the first invention group will next be described.

When a specific alkali metal compound is added to a crude 1,3-butylene glycol or a bottom product which is produced through the aforementioned conventional process and is subjected to distillation (distillation for removal of high-boiling-point substances) for removing high-boiling-point substances, and the resultant 1,3-butylene glycol is subjected to heating treatment, substances causing odor can be effectively reduced, and 1,3-butylene glycol which undergoes minimal change in quality with passage of time can be obtained.

Since the crude 1,3-butylene glycol or 1,3-butylene glycol as a bottom product after distillation for removal of high-boiling-point substances contains small amounts of high-boiling-point substances, even when the 1,3-butylene glycol is heated with an alkali, no amount or a very small amount of low-boiling-point substances is produced through decomposition of high-boiling-point substances. Briefly, the amount of low-boiling-point substances causing odor is effectively reduced through reaction with an alkali. As a result, the absolute amount of low-boiling-point substances can be reduced to about zero. Therefore, 1,3-butylene glycol of very high purity which issues no odor and undergoes a minimal change in quality with passage of time can be produced.

The 1,3-butylene glycol of the present invention exhibits potassium permanganate color-fading time of at least 15 minutes, preferably at least 25 minutes, more preferably at least 35 minutes, as measured according to JIS K1351 3.10 immediately after production, and exhibits potassium permanganate color-fading time of at least 5 minutes, preferably at least 10 minutes, more preferably at least 20 minutes, as measured according to JIS K1351 3.10 at a period of three months after production. The 1,3-butylene glycol is characterized by issuing very reduced odor and producing minimal change in quality with passage of time. The color-fading time of the 1,3-butylene glycol after storage can be measured at any time, so long as at least three months have elapsed after production.

FIG. 1 is a flowsheet showing an embodiment for producing a 1,3-butylene glycol of high purity of the first invention group. Reference numeral 1-1 represents a dehydration tower, 1-2 is a salt-removal tower (thin-film evaporator), 1-3 is a distillation tower for removal of high-boiling-point substances, 1-4 is an alkali reactor, 1-5 is an alkali-removal tower (thin-film evaporator), and 1-6 is a final product distillation tower.

Crude 1,3-butylene glycol which has been subjected to distillation for removing high-boiling-point substances is fed into the alkali reactor (e.g., a flow-type tubular reactor) 1-4. Simultaneously, an alkali metal compound is added to the crude 1,3-butylene glycol in an amount of 0.05–10% by weight, preferably 0.1–1.0% by weight, on the basis of the entirety of the butylene glycol. When the amount of the alkali metal compound added to the crude butylene glycol is 10% by weight or more, the alkali metal compound is precipitated in, for example, a distillation tower or a feed pipe, to thereby cause clogging, which is not preferable. In addition, when the amount of the alkali metal compound added is very large, decomposition of high-boiling-point substances proceeds, resulting in generation of substances causing odor. In contrast, when the amount of the alkali metal compound added is less than 0.05% by weight, the effect of the compound on substances causing odor is lowered, which are not preferable. The 1,3-butylene glycol is fed into the alkali reactor 1-4.

In the purification process for the 1,3-butylene glycol, the alkali metal compound to be added must be at least one compound of sodium hydroxide and potassium hydroxide. The alkali metal compound may be added in the form of a solid. However, from a viewpoint of operation and in order to facilitate bringing the alkali metal compound into contact with a target solution easily, the compound is preferably added in the form of an aqueous solution.

In the alkali reactor 1-4, the reaction temperature is 90–140° C., preferably 110–130° C. This is because, when the reaction temperature is low, reaction residence time becomes long, requiring a reactor of large capacity, which is not economical, whereas when the reaction temperature is high, the odor of the 1,3-butylene glycol is impaired. The reaction residence time is 5–120 minutes, preferably 10–30 minutes. When the residence time is short, the reaction proceeds insufficiently, and the quality of a final product is impaired, whereas when the residence time is long, a reactor of large capacity is required, resulting in high equipment cost, which is disadvantageous from the viewpoint of economics.

It is to be noted that the crude 1,3-butylene glycol fed into the alkali reactor may be any type of a crude 1,3-butylene glycol, so long as the butylene glycol has been subjected to distillation for removing high-boiling-point substances. For example, the crude butylene glycol may be even a product 1,3-butylene glycol obtained from the bottom of the product distillation tower employed in the aforementioned conventional process.

The resultant crude reaction mixture is discharged from the alkali reactor 1-4, and then fed into the alkali-removal tower (thin-film evaporator) 1-5. The alkali metal compound used for the reaction is removed from the bottom of the tower. The evaporator to be employed as the alkali-removal tower is appropriately a naturally falling-type thin film evaporator realizing short residence time or a forcibly stirring-type thin-film evaporator, in order to suppress thermal history of a process fluid.

In the evaporator, evaporation is carried out under a reduced pressure of 100 torr or less, preferably 5–20 torr, as measured at the top of the evaporator. In order to reduce the odor of 1,3-butylene glycol, the distillation (evaporation) temperature is preferably lower, and the pressure is preferably lower. When distillation is carried out under the aforementioned conditions, the temperature of the evaporator is maintained at 90–120° C. The added alkali metal compound is removed from the bottom of the evaporator together with high-boiling-point substances. 1,3-Butylene glycol containing low-temperature-point substances is obtained as a distillate from the top of the evaporator and then fed into the final product distillation tower.

The final product distillation tower may be a perforated plate tower or a bubble-cap tower. Preferably, the final product distillation tower is a packed tower of low pressure loss which is packed with Sluzer Packing or Melapack (a trade name of Sumitomo Heavy Industries, Ltd.). Such a packed tower is used in order to reduce the distillation temperature to as low as possible, since 1,3-butylene glycol is thermally decomposed at 200° C. or higher, and adverse effects in relation to odor are obtained (Japanese Patent Application Laid-Open (kokai) No. 63-156738). Similarly, when the thermal history (residence time) of 1,3-butylene glycol is long, adverse effects are obtained. Therefore, a reboiler to be employed is appropriately a thin-film evaporator realizing short residence time of a process fluid, such as a naturally falling-type thin film evaporator or a forcibly stirring-type thin-film evaporator.

The theoretical plate number of the final product distillation tower varies with the concentration of low-boiling-point substances contained in the solution fed into the tower. When the concentration of low-boiling-point substances contained in the solution fed into the tower is 5% or less, the theoretical plate number of the tower is about 10–20. The solution is preferably fed to a position 20–70% of the height of the tower distant from the top of the tower. Distillation is carried out under a reduced pressure of 100 torr or less, preferably 5–20 torr, as measured at the top of the tower. In order to reduce the order of the 1,3-butylene glycol, the distillation temperature is preferably lower, and the pressure is preferably lower. Distillation is preferably carried out at a reflux ratio of 0.5–2.0.

As shown in FIG. 1, the solution obtained by condensing the vapor from the alkali-removal tower in the condenser 1-5-2 is fed into the final product distillation tower. However, in order to reduce the amount of steam for heating the final product distillation tower, the vapor from the top of the alkali-removal tower may be fed directly into the product distillation tower. 1,3-Butylene glycol as a product is obtained from the bottom of the final product distillation tower. The thus-obtained 1,3-butylene glycol exhibits sufficiently long potassium permanganate color-fading time as measured according to JIS K1351 3.10; i.e, the 1,3-butylene glycol of high purity contains very small amounts of reducing substances, etc., issues no odor, and undergoes a minimal change in quality with passage of time.

Characteristic features of the second invention group will next be described.

In the second invention group, the hydrogen source material, the step preceding hydrogenation which is carried out according to needs, and the hydrogen which is employed are similar to those described in the first invention group.

In the second invention group, a catalyst used for hydrogenation (the catalyst may be referred to as "hydrogenation catalyst") is a Raney nickel having a specific hydrogenation activity.

The Raney nickel to be employed contains nickel in an amount of about 50% by weight during alloying, contains aluminum in an amount of less than 10% by weight after development, and exhibits the following acetone hydrogenation activity and/or phenol hydrogenation activity.

(i) The acetone hydrogen activity is at least 2,000 ml/g-Ni/hr, preferably at least 3,000 ml/g-Ni/hr, more preferably at least 4,000 ml/g-Ni/hr.

When the acetone hydrogenation activity is less than 2,000 ml/g-Ni/hr, it is difficult to efficiently obtain 1,3-butylene glycol of reduced odor from a hydrogenation crude mixture through distillation.

The term "acetone hydrogenation activity" refers to the hydrogen absorption rate by acetone as measured for a period of from five minutes to 30 minutes after initiation of hydrogenation of the acetone, which is carried out at 25° C. and ambient pressure after wet a Raney nickel (0.3 g) is added to acetone (50 ml). The acetone hydrogenation activity is represented by hydrogen absorption amount (unit: ml/g-Ni/hr). The accurate amount of nickel contained in the wet Raney nickel is obtained through analysis after the hydrogenation.

(ii) The phenol hydrogenation activity is at least 500 ml/g-Ni/hr, preferably at least 800 ml/g-Ni/hr, more preferably at least 1,100 ml/g-Ni/hr.

When the phenol hydrogenation activity is less than 500 ml/g-Ni/hr, it is difficult to efficiently obtain 1,3-butylene glycol of reduced odor from a hydrogenation crude mixture through distillation.

The term "phenol hydrogenation activity" refers to the hydrogen absorption rate by phenol as measured for a period of from five minutes to 30 minutes after initiation of hydrogenation of the phenol, which is carried out at 50° C. and ambient pressure after a wet Raney nickel (0.5 g) is added to a solution mixture of phenol and cyclohexanol (volume ratio 7:3) (60 ml). The phenol hydrogenation activity is represented by hydrogen absorption amount (unit: ml/g-Ni/hr). The accurate amount of nickel contained in the wet Raney nickel is obtained through analysis after the hydrogenation.

Hydrogenation Step

Hydrogenation is carried out through the reaction process under the reaction conditions described in the first invention group. Hydrogenation is carried out such that the amount of the aldehyde groups remaining in a hydrogenation crude mixture becomes 200 ppm by weight or less, preferably 50 ppm by weight or less, more preferably 20 ppm by weight or less, much more preferably 10 ppm by weight or less.

Purification Step after Hydrogenation

A hydrogenation crude mixture is subjected to a treatment, such as distillation for removal of alcohols, dehydration distillation, evaporation, removal of impurities, chemical treatment of a remaining double bond, or a combination thereof.

The distillation for removal of alcohols is carried out for removing generated alcohols such as ethanol, isopropanol, and butanol.

The dehydration distillation is carried out for removing generated water and for subjecting impurities to azeotropic distillation with water.

The evaporation is carried out for removing neutralized products of the hydrogenation catalyst or a base, which are generated, for example, in the condensation step, and thermally-decomposable high-boiling-point substances. Evaporation is carried out by means of an evaporation operation of short heating residence time, such as single distillation or flash distillation.

The chemical treatment of a remaining double bond is carried out by adding, for example, a hydroxide alkali or ozone to a double bond, particularly a double bond which reacts in the chameleon test (potassium permanganate solution color-fading time as measured according to JIS K1351 3.10), by cleaving the double bond, or by reducing the double bond with, for example, sodium borohydride.

The removal of impurities is carried out for removing other low-boiling-point substances such as butanone and high-boiling-point substances, and is carried out by means of, for example, distillation, adsorption, or ion exchange.

The distillation method is not particularly limited, so long as low-boiling-point substances and high-boiling-point substances can be separated from 1,3-butylene glycol by utilizing the difference in boiling point between the 1,3-butylene glycol and the substances. Examples of the distillation method to be employed include reduced-pressure distillation, ambient-pressure distillation, compressed distillation, azeotropic distillation, extracting distillation, and reactive distillation.

No particular limitation is imposed on the types of the purification processes after hydrogenation and the order of the processes. For example, removal of alcohols, azeotropic dehydration for removal of low-boiling-point substances, evaporation, removal of high-boiling-point substances through distillation of 1,3-butylene glycol, and removal of low-boiling-point substances through distillation are carried out successively, to thereby produce a purified 1,3-butylene glycol.

A characteristic feature of the second invention group resides in that acetaldols are hydrogenated by use of a Raney nickel catalyst having a specific hydrogenation activity, the resultant hydrogenation crude mixture is subjected to distillation to thereby separate low-boiling-point components (L), and then the resultant mixture is further subjected to distillation, to thereby yield 1,3-butylene glycol as a distillate.

Examples of the low-boiling-point components (L) include alcohols such as the aforementioned ethanol, isopropanol, and butanol; water; impurities which are azeotropically distilled with moisture and water; and other low-boiling-point substances.

Therefore, in order to separate the low-boiling-point components (L), distillation for removal of alcohols, dehydration distillation, and distillation for removal of other low-boiling-point substances may be carried out separately, or a single distillation operation may be carried out. Usually, when a valuable product such as ethanol or butanol is recovered, distillation for removal of ethanol and distillation for removal of butanol may be carried out separately. In order to further reduce odor, dehydration distillation may be carried out after distillation for removal of alcohols.

When the hydrogenation crude mixture is subjected to distillation to thereby yield 1,3-butylene glycol as a distillate, the catalyst, neutralized salts, and high-boiling-point substances, including thermally decomposable high-boiling-point substances, which are contained in the crude mixture, are impaired, and a component which is distilled together with the 1,3-butylene glycol is produced, the component causing lowering of purity, odor, coloring of the butylene glycol, etc. Therefore, in order to separate the catalyst, the neutralized salts, and the high-boiling-point substances including thermally decomposable high-boiling-point substances, the aforementioned evaporation treatment can be carried out after separation of the low-boiling-point components (L).

After the evaporation treatment, the resultant hydrogenation crude mixture can be subjected to distillation, to thereby obtain a purified 1,3-butylene glycol as a distillate.

In order to further reduce odor, the 1,3-butylene glycol distillate may further be subjected to distillation, to thereby separate low-boiling-point components (1).

The term low-boiling-point components (1) refers to an impurity contained in the 1,3-butylene glycol distillate. Examples of the low-boiling-point components (1) include a minor amount of alcohols, such as ethanol, isopropanol, and butanol; water; and other low-boiling-point substances.

After the evaporation treatment, the hydrogenation crude mixture may be subjected to distillation, to thereby separate the low-boiling-point components (1). Preferably, after the evaporation treatment, 1,3-butylene glycol is obtained as a distillate, and the 1,3-butylene glycol distillate is subjected to distillation, to thereby separate the low-boiling-point components (1).

Thus, the purified 1,3-butylene glycol of reduced odor can be produced reliably and efficiently.

Quantification of Remaining Aldehyde Group

In the present invention, the amount of aldehyde groups remaining in the hydrogenation crude mixture, the aldehyde groups being considered to be a substance causing odor, is quantified, and the hydrogenation process can be controlled.

Examples of the method for quantifying the content of aldehyde groups include a hydroxylamine hydrochloride method in which hydroxylamine hydrochloride is added to the hydrogenation crude mixture and a liberated hydrogen chloride component is quantified.

Examples of the method for quantifying the hydrogen chloride component include a method in which an indicator, such as, Bromophenol Blue (BPB), is added and discoloration time is measured.

Hereinafter, a method in which the BPB is added to a hydrogen chloride component which is liberated by adding hydroxylamine hydrochloride (HA.HCl) to the hydrogenation crude mixture and discoloration time is measured will be abbreviated as "HA.HCl-BPB method."

Hydroxylamine Hydrochloride-Bromophenol Blue (HA.HCl-BPB) Method

Usually, hydroxylamine hydrochloride (HA.HCl) reacts with carbonyl compounds such as aldehyde and ketone as follows, to thereby liberate hydrochloric acid.

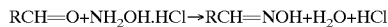

$$RCH=O + NH_2OH.HCl \rightarrow RCH=NOH + H_2O + HCl$$

The indicator BPB discolors by the liberated hydrochloric acid. The discoloration is quantified by means of colorimetry by visual observation or by use of a colorimeter. In the present invention, the hydrogenation process and distillation conditions can be monitored by means of colorimetry by visual observation, instead of through direct measurement of the content of aldehyde groups. Therefore, such colorimetry falls within the meaning of the method for quantifying the content of remaining aldehyde groups.

HA.HCl-BPB Method

The method for quantifying the content of aldehyde groups remaining in the hydrogenation crude mixture relating to the present invention is carried out as follows.

Preparation of <0.1% BPB Solution>

BPB (0.1 g) and ethanol (20 ml) are added to a 100-ml messflask and dissolved, and distilled water is added to the messflask until the level of the water reaches an indicator of the messflask.

Preparation of <BPB-Added Hydroxylamine Hydrochloride Solution>

(1) Hydroxylamine hydrochloride (69.5 g) is added to a 1-liter messflask, the 0.1% BPB solution (25 ml) is added to the messflask, and pure water is added to the messflask until the level of the water reaches the indicator of the messflask.

(2) A 1/10N-NaOH aqueous solution is added to the solution prepared in (1), to thereby adjust the pH of the solution to 3.5.

(Analysis Operation)

(1) The hydrogenation crude mixture (5 ml) after filtration of the catalyst is sampled in a test tube.

(2) The above-prepared BPB-added hydroxylamine hydrochloride solution (5 ml) is added to the sampled solution, and mixed therewith, to thereby prepare a test solution.

(3) The time required for changing the color of the test solution from blue or yellow-green into yellow is measured as discoloration time.

When acetaldol was used as a sample, and discoloration time was measured. The correlation between the content of aldehyde groups and discoloration time is described below. The content of aldehyde groups is obtained by the following formula: the content of aldehyde groups=the content of acetaldol×29.1/88.1.

TABLE 2-1

| Content of aldehyde groups (ppm by weight) | Discoloration time (hour) |
| --- | --- |
| 200 | 1.1 |
| 50 | 4.2 |
| 20 | 8.2 |
| 10 | 16.3 |

The quality of the hydrogenation crude mixture correlates to the content of aldehyde groups remaining in the mixture. As described below, the quality of the hydrogenation crude mixture can be determined by the length of discoloration time when the BPB-added hydroxylamine hydrochloride solution is added to the mixture.

(1) In the case of good quality: blue→yellow-green→yellow (time required for changing the color of the mixture from blue to yellow-green is long.)

(2) In the case of poor quality: blue→yellow-green→yellow (time required for changing the color of the mixture from blue to yellow-green is short.)

(3) In the case of very poor quality: the color of the mixture becomes yellow immediately after addition of the BPB-added hydroxylamine hydrochloride solution.

The correlation between the aforementioned discoloration time and the distillation process for obtaining a purified 1,3-butylene glycol which issues no odor or considerably reduced odor is summarized below on the basis of the results of actual operations.

TABLE 2-2

| Discoloration time of hydrogenation crude mixture | Quality of hydrogenation crude mixture | Effects on distillation |
| --- | --- | --- |
| 16 hours or more | Good | 1,3-BG issues no odor cut percentage: possible to reduce |
| 8–16 hours | Fair | 1,3-BG issues a reduced odor cut percentage: fair |
| 4–8 hours | Slightly poor | 1,3-BG issues a slight odor cut percentage: slightly increased |
| 1–4 hours | Poor | 1,3-BG issues an odor (not passed) cut percentage: increased |
| Less than 1 hour | Very poor | 1,3-BG issues an odor (not passed) cut percentage: very increased |

It is to be noted that the cut percentage described in the aforementioned correlation is the cut percentage of low-boiling-point-substances and/or high-boiling-point substances. The cut percentage correlates to the separation plate number of the distillation tower and the reflux ratio. When the separation plate number and the reflux ratio are increased, the cut percentage can be reduced, but facility costs or costs for utilities such as steam are increased.

The discoloration time is at least one hour, preferably at least four hours, more preferably at least eight hours, much more preferably at least 16 hours. When the discoloration time is less than one hour, the cut percentage is drastically increased in order to obtain a purified 1,3-butylene glycol which issues a considerably reduced odor, and thus productivity is lowered considerably.

The purified 1,3-butylene glycol produced through the process of the second invention group is used as an intermediate material for producing a solvent for paints and various compounds. Also, the 1,3-butylene glycol can be used as a raw material for cosmetics such as a humectant and as an additive for animal feeds, since the 1,3-butylene glycol has high purity and does not issue any problematic odor or exhibit any disagreeable taste.

According to the second invention group, control of the process is rationalized, the yield of the purified 1,3-butylene glycol which issues no odor or a considerably reduced odor is enhanced, costs for utilities are reduced, and 1,3-butylene glycol of reduced odor can be produced efficiently and reliably.

Characteristic features of the third invention group will next be described.

Aldols obtained through condensation of acetaldehyde in the presence of a basic catalyst have been defined in connection with the first invention group.

In the third invention group, an acid is added to a mixture produced in an aldehyde condensation step (the mixture may be referred to as "crude reaction mixture") so as to acidify the mixture, and the resultant mixture is used as a raw material for hydrogenation. As described in connection with the first invention group, at least a portion of unreacted acetaldehyde is removed from the hydrogenation raw material, since the unreacted acetaldehyde is usually recycled in the condensation step. However, the raw material for hydrogenation may contain residual acetaldehyde, crotonaldehyde, small amounts of aldehyde components, low-boiling-point substances, high-boiling-point substances such as aldehyde dimers and aldehyde trimers, and water. A raw material for hydrogenation containing water in an amount of 10–20% by weight can be used. A raw material for hydrogenation having a purity of 95–98% by weight based on acetaldol components, exclusive of water, is preferably used.

Acidification of the produced mixture may be carried out after neutralization following condensation of acetaldehyde, or may be carried out after thermal decomposition of aldoxane. Preferably, after thermal decomposition of aldoxane is carried out in a neutral atmosphere, the produced mixture is acidified immediately before hydrogenation so as to attain a predetermined acidity. Thus, by-production of crotonaldehyde—which is by-produced through dehydration in an acidic state during thermal decomposition of aldoxane—can be reduced.

Examples of the aforementioned acid include organic acids and inorganic acids. Examples of the inorganic acids include phosphoric acid and monoalkyl or dialkyl esters of phosphoric acid. Organic acids are preferred. Examples of the organic acids include monocarboxylic acids such as formic acid, acetic acid, and propionic acid; and dicarboxylic acids such as oxalic acid, malonic acid, succinic acid, maleic acid, and tartaric acid. Monocarboxylic acids are more preferred, with acetic acid being particularly preferred.

100% Acetic acid may be used, but, in order to facilitate neutralization and acidification operations, for example, a 5–20% by volume acetic acid aqueous solution is used.

The acidity of the raw material for hydrogenation is 1–30, preferably 2–10. Herein, the acidity refers to an amount (ml) of a 1/10 N sodium hydroxide aqueous solution to be required for neutralizing 100 ml of a sample (indicator: phenolphthalein).

In the third invention group, since the acidity of the mixture subjected to hydrogenation falls within the above range, impairment of a catalyst during the hydrogenation step—which is attributed to, for example, generation of polymers—can be prevented. When the acidity is below the above range, prevention of catalyst impairment is unsatisfactory, whereas when the acidity exceeds the above range, the by-production percentage of butanol is increased, which is attributed to by-production of crotonaldehyde, or corrosion of an apparatus employed in the hydrogenation step proceeds.

Step Preceding Hydrogenation

The raw material for hydrogenation and the treatment method thereof are similar to those described in connection with the first invention group, except that, in the third invention group, there is employed a crude reaction mixture which has been adjusted to have an acidity of a predetermined range.

The hydrogen and the catalyst used for hydrogenation are similar to those described in connection with the first invention group.

Hydrogenation Step

As described in connection with the first invention group, hydrogenation is carried out such that the content of the aldehyde groups remaining in a hydrogenation crude mixture becomes 200 ppm by weight or less, preferably 50 ppm by weight or less, more preferably 20 ppm by weight or less, much more preferably 10 ppm by weight or less. In the third invention group, the acidity of the mixture is maintained so as to fall within the aforementioned range during hydrogenation.

Production Step after Hydrogenation Reaction

As described in connection with the purification step after hydrogenation reaction of the second invention group, a hydrogenation crude mixture is subjected to a treatment, such as distillation for removal of alcohols, dehydration distillation, evaporation, removal of impurities, chemical treatment of remaining double bonds, or a combination thereof. The subsidiary description of these treatments has been provided in connection with the purification step after hydrogenation of the second invention group.

1,3-Butylene glycol produced through the process of the third invention group is used as an intermediate material for producing a solvent for paints and various compounds. Also, the 1,3-butylene glycol can be used as a raw material for cosmetics such as a humectant, and as an additive for animal feed, since the 1,3-butylene glycol has high purity and does not issue any problematic odor or exhibit any disagreeable taste.

Characteristic features of the fourth invention group will next be described.

Aldols produced through condensation of acetaldehyde have been described in connection with the first invention group. A mixture produced in an acetaldehyde condensation step is usually neutralized with an acid in the subsequent neutralization step, and the resultant mixture is used as a raw material for hydrogenation. The crude reaction mixture used in the hydrogenation step may be even neutral. However, when the mixture is acidified with acetic acid so as to attain an acidity of 1–30, preferably 2–10, there can be prevented impairment of a catalyst which is attributed to generation of polymers in the hydrogenation step (hydrogenation reaction), or there can be prevented by-production of butanol, etc. which is attributed to by-production of crotonaldehyde, etc. The aforementioned raw material for hydrogenation has been defined in connection with the first invention group. Acidification of the crude reaction mixture by use of an organic acid or inorganic acid in the hydrogenation step and the acidity of the mixture have been described in connection with the third invention group.

Step Preceding Hydrogenation

The raw material for hydrogenation and the treatment method thereof are similar to those described in connection with the first invention group, except that, in the fourth invention group, there is employed a crude reaction mixture of aldehyde condensation reaction which has been adjusted to have an acidity of a predetermined range. Further, hydrogen and catalysts to be employed for hydrogenation are also described in the first invention group.

Hydrogenation Step

As described in connection with the first invention group, hydrogenation is carried out such that the content of the aldehyde groups remaining in a hydrogenation crude mixture becomes 200 ppm by weight or less, preferably 50 ppm by weight or less, more preferably 20 ppm by weight or less, much more preferably 10 ppm by weight or less. In the present invention (the fourth invention group), the acidity of the mixture is maintained so as to fall within the aforementioned range during hydrogenation.

Production Step after Hydrogenation Reaction

As described in connection with the purification step after hydrogenation of the second invention group, a hydrogenation crude mixture is subjected to a treatment, such as distillation for removal of alcohols, dehydration distillation, evaporation, removal of impurities, chemical treatment of remaining double bond, or a combination thereof. The subsidiary description of these treatments has been provided in connection with the purification step after hydrogenation of the second invention group.

In the fourth invention group, after low-boiling-point substances such as alcohols are removed from the hydrogenation crude mixture, the resultant mixture is optionally subjected to dehydration distillation and evaporation, to thereby remove from the mixture neutralized salts, the catalyst, and thermally decomposable high-boiling-point substances, and the resultant mixture is subjected to distillation, to thereby yield 1,3-butylene glycol as a distillate.

However, when alcohols, etc. are distilled off from the acidic hydrogenation crude mixture, ethers are generated from alcohols or 1,3-butylene glycol through heating, and thus the yield of 1,3-butylene glycol is reduced, and the quality of the purified 1,3-butylene glycol is lowered, which is attributed to contamination of ethers.

Therefore, in the present invention (the fourth invention group), the hydrogenation crude mixture is basified, and then removal of alcohols through distillation, or evaporation is carried out. The hydrogenation crude mixture may be basified immediately after hydrogenation, after removal of ethanol, after removal of butanol, or after dehydration distillation. Preferably, the hydrogenation crude mixture is basified immediately after hydrogenation.

The basified hydrogenation crude mixture has a pH of 9–12, preferably 10 or more, more preferably 11.0–11.5.

When the hydrogenation crude mixture is acidic, ethers are generated. When the hydrogenation crude mixture is neutral or has a pH of less than 9, the yield or odor of 1,3-butylene glycol is not satisfactorily improved. On the other hand, when the hydrogenation crude mixture has a pH of more than 12, thermally decomposable high-boiling-point substances are decomposed to generate components causing odor or coloring, and thus the quality of purified 1,3-butylene glycol is lowered.

The hydrogenation crude mixture is basified through use of, for example, lithium hydroxide, sodium hydroxide, potassium hydroxide, calcium hydroxide, magnesium hydroxide, or amines. Preferably, sodium hydroxide or potassium hydroxide is used for basification. More preferably, sodium hydroxide is used.

In order to facilitate addition of sodium hydroxide to the hydrogenation crude mixture, sodium hydroxide is used in the form of an aqueous solution. A 5–50% by weight sodium hydroxide aqueous solution is used.

A 1,3-butylene glycol distillate obtained through distillation can be used as a final product. In accordance with use, distillation of the distillate is further carried out, to thereby separate remaining low-boiling-point components.

1,3-Butylene glycol produced through the process of the fourth invention group is used as an intermediate material for producing a solvent for paints and various compounds. Also, the 1,3-butylene glycol can be used as a raw material for cosmetics such as a humectant, and as an additive for animal feeds, since the 1,3-butylene glycol has high purity and does not issue any problematic odor or exhibit any disagreeable taste.

Characteristic features of the fifth invention group will next be described.

Aldols produced through condensation of acetaldehyde have been described in connection with the first invention group. A mixture produced in an acetaldehyde condensation step is usually neutralized with an acid in the subsequent neutralization step, and the resultant mixture is used as a raw material for hydrogenation. The crude reaction mixture used in the hydrogenation step may be even neutral. However, when the mixture is acidified with acetic acid so as to attain an acidity of 1–30, preferably 2–10, there can be prevented impairment of a catalyst which is attributed to generation of polymers in the hydrogenation step (hydrogenation reaction), or there can be prevented by-production of butanol, etc. which is attributed to by-production of crotonaldehyde, etc. The aforementioned raw material for hydrogenation has been defined in connection with the first invention group. Acidification of the crude reaction mixture by use of an organic acid or inorganic acid in the hydrogenation step and the acidity of the mixture have been described in connection with the third invention group.

Step Preceding Hydrogenation

The raw material for hydrogenation and the treatment method thereof are similar to those described in connection with the first invention group, except that, in the fifth invention group, there is employed a crude reaction mixture which has been adjusted to have an acidity of a predetermined range.

Further, the hydrogen and the catalyst used for hydrogenation are similar to those described in connection with the first invention group.

Hydrogenation Step

As described in connection with the first invention group, hydrogenation is carried out such that the content of the aldehyde groups remaining in a hydrogenation crude mixture becomes 200 ppm by weight or less, preferably 50 ppm by weight or less, more preferably 20 ppm by weight or less, much more preferably 10 wt. ppm or less. In the fifth invention group, the acidity of the mixture is maintained so as to fall within the aforementioned range during hydrogenation.

Production Step after Hydrogenation

As described in connection with the purification step after hydrogenation of the second invention group, a hydrogenation crude mixture is subjected to a treatment, such as distillation for removal of alcohols, dehydration distillation, evaporation, removal of impurities, chemical treatment of remaining double bond, or a combination thereof. The subsidiary description of these treatments has been provided in connection with the purification step after hydrogenation of the second invention group.

A characteristic feature of the fifth invention group resides in that, after distillation of the hydrogenation crude mixture is carried out to thereby separate low-boiling-point components (L), the resultant mixture is subjected to distillation to thereby yield 1,3-butylene glycol as a distillate, and the distilled 1,3-butyelen glycol (D) is treated with ozone.

Examples of the low-boiling-point components (L) include aldohols such as the aforementioned ethanol, isopropanol, and butanol; water; impurities which are azeotropically distilled together with moisture and water; and other low-boiling-point substances.

Therefore, in order to separate the low-boiling-point components (L), distillation for removal of alcohols, dehydration distillation, and distillation for removal of other low-boiling-point substances may be even carried out separately, or a single distillation operation may be even carried out. Usually, when an organic product such as ethanol or butanol is recovered, distillation for removal of ethanol and distillation for removal of butanol may be carried out separately. Further, in order to further reduce odor, dehydration distillation may be carried out after distillation for removal of alcohols.

When distillation of the hydrogenation crude mixture is carried out to thereby yield 1,3-butylene glycol as a distillate, thermally decomposable high-boiling-point substances contained in the crude mixture are impaired, and a component which is distilled together with the 1,3-butylene glycol is produced, the component causing lowering of purity, generation of odor, and coloring of the butylene glycol. Therefore, in order to separate salts, the catalyst, and high-boiling-point substances including the thermally decomposable high-boiling-point substances, the aforementioned evaporation treatment can be carried out after separation of the low-boiling-point components (L). After the evaporation treatment, the resultant hydrogenation crude mixture is subjected to distillation, to thereby obtain 1,3-butylene glycol as a distillate (D).

Ozone Treatment

During ozone treatment, impurities such as substances causing odor undergo chemical change, including decomposition and deodorization.

Ozone (1 mg–1 g, preferably 10 mg–0.5 g) is added to 1 kg of the 1,3-butyele glycol distillate (D), and is brought into contact with the distillate at a temperature equal to or lower than the oxidation limit temperature of 1,3-butylene glycol, preferably at a temperature between ambient temperature and 60° C., for 0.1–6 hours, preferably 0.5–2 hours, to thereby carry out ozone treatment.

When the amount of added ozone is below the above range, the treatment proceeds insufficiently, and thus reduction of substances causing odor, etc. is difficult, whereas when the amount of added ozone exceeds the above range, costs required for the treatment increase, or side reaction is caused.

In order to bring ozone into contact with the 1,3-butylene glycol distillate (D), an ozone-containing gas is blown into the distillate, or the ozone-containing gas is involved in the distillate with stirring. When convenience is an important consideration, the ozone-containing gas is blown into the distillate.

For example, while the 1,3-butylene glycol distillate (D) is continuously fed into a reactor, the ozone-containing gas is continuously fed through the bottom of the reactor, and an ozone-treated 1,3-butylene glycol is discharged from the top of the reactor.

The reactor is not particularly limited, and a conventional gas-liquid contact-type reactor may be used. Gas-liquid contact process may employ a method in which a liquid is fed through the bottom of the reactor and the ozone-containing gas is fed through the bottom thereof, or a method in which a liquid is fed through the top of the reactor and ozone-containing gas is fed through the bottom thereof. The resultant reaction mixture may be also circulated.

Ozone is generated through silent discharge by use of an ozone generator to which air or oxygen is supplied, or through electrolysis of a sulfuric acid aqueous solution.

In the case of silent discharge of air, 0.1–10% by weight of ozone can be generated. 10–30% by weight of ozone can be generated by carrying out electrical discharge while the ozone generator is cooled with liquid air.

When a sulfuric acid-aqueous solution having a specific gravity of 1.1–1.4 is used, about 20% by weight of ozone can be generated through electrolysis.

If necessary, nitrogen, carbon dioxide, or air may be blown into the ozone-treated 1,3-butylene glycol to thereby purge remaining ozone, and the resultant 1,3-butylene glycol may be stored.

Separation of Low-Boiling-Point Components (1)

In order to obtain 1,3-butylene glycol of further high purity, low-boiling-point components (1) are separated from the ozone-treated 1,3-butylene glycol. The term low-boiling-point components (1) refers to low-boiling-point components contained in the ozone-treated 1,3-butylene glycol. Specific examples of the low-boiling-point components (1) include low-boiling-point substances which exist in 1,3-butylene glycol after hydrogenation, such as small amounts of the low-boiling-point components (L) remaining in the 1,3-butylene glycol; and low-boiling-point substances generated through the ozone treatment.

Examples of the method for separating the low-boiling-point components (1) include a method in which the ozone-treated 1,3-butylene glycol is fed into a distillation tower, and the low-boiling-point components (1) are distilled from the tower through distillation; a method in which the ozone-treated 1,3-butylene glycol is subjected to topping by means of heating; a method in which the ozone-treated 1,3-butylene glycol is subjected to bubbling by blowing nitrogen, carbon dioxide, air, etc. through the bottom of a distillation tower; a method in which heated steam is blown into a distillation tower and the low-boiling-point components (1) are discharged together with the steam; a method in which heated 1,3-butylene glycol is fed into a reduced-pressure chamber and the low-boiling-point components (1) are subjected to flash distillation; a method employing membrane separation; a method employing adsorption; and a combination of these methods. These methods may be carried out at ambient pressure or under reduced pressure.

Purified 1,3-butylene glycol produced through the process of the fifth invention group is used as an intermediate material for producing a solvent for paints and various compounds. Also, the 1,3-butylene glycol can be used as a raw material for cosmetics such as a humectant, and as an additive for animal feeds, since the 1,3-butylene glycol has high purity and does not issue any problematic odor or exhibit any disagreeable taste.

Characteristic features of the sixth invention group will next be described.

The sixth invention group provides a process for producing butanol, which includes, when acetaldols are synthesized from acetaldehyde and the acetaldols are hydrogenated, hydrogenating, during a hydrogenation step, crotonaldehyde which is by-produced during synthesis of the acetaldols to thereby allow by-production of butanol; subjecting the by-produced butanol to distillation for separating impurities; and subjecting the resultant butanol to chemical treatment, and then to distillation. The sixth invention group also provides a process for producing butyl acetate from the above-produced butanol and acetic acids.

When 1,3-butylene glycol is produced from acetaldehyde serving as a starting material, during condensation of acetaldehyde in the presence of a basic catalyst, acetaldols are produced and a small amount of crotonaldehyde is by-produced. Acetaldols have been defined in connection with the first invention group.

As described in connection with the first invention group, a mixture of acetaldehyde and paraldols produced through thermal decomposition of aldoxane can be used, and crotonaldehyde is further by-produced during the thermal decomposition.

During synthesis of acetaldol, crotonaldehyde (1–10% by weight, usually 2–5% by weight) and other by-products (about 1–5% by weight) are by-produced.

A solution produced through synthesis of acetaldols is provided in the hydrogenation step described hereinafter, and the solution is hydrogenated in the presence of a catalyst.

It is to be noted that in the sixth invention group, after synthesis of acetaldols, when a large amount of unreacted acetaldehyde is recovered through distillation and the acetaldehyde is recycled in the condensation step, a portion of crotonaldehyde can be separated and recovered. The separated and recovered crotonaldehyde is added to acetaldols, which is a bottom solution when acetaldehyde is recovered through distillation, and the recovered crotonaldehyde and crotonaldehyde remaining in the bottom solution may be utilized for by-production of butanol in a hydrogenation step.

Hydrogenation Step

The thus-produced acetaldols and crotonaldehyde are provided to a hydrogenation step together with non-recovered acetaldehyde, other by-products, and water, etc.

The hydrogen, catalyst, and apparatus employed in hydrogenation of acetaldols, the reaction temperature, and the reaction pressure have been described in connection with the first invention group.

Hydrogenation is carried out such that the content of the aldehyde groups remaining in a hydrogenation reaction crude mixture (which may be referred to as "hydrogenation crude mixture) becomes 200 ppm by weight or less, preferably 50 ppm by weight or less.

After hydrogenation reaction, the catalyst is separated from the hydrogenation crude mixture. The resultant hydrogenation crude mixture contains 1,3-butylene glycol, butanol, isopropyl alcohol, ethanol, water, other low-boiling-point substances, and other high-boiling-point substances, and the crude mixture is provided to a purification step.

Purification Step

The resultant hydrogenation crude mixture is subjected to distillation, to thereby yield a distillate (A) and obtain 1,3-butylene glycol and large amounts of high-boiling-point substances as bottom products. The distillate (A) contains butanol, ethanol, water, other low-boiling-point substances, a small amount of 1,3-butylene glycol, and small amounts of other high-boiling-point substances.

The bottom solution containing 1,3-butylene glycol is further purified, to thereby yield 1,3-butylene glycol as a final product.

Butanol Purification Step

On the other hand, the distillate (A) is further subjected to distillation, to thereby separate, as a distillate, low-boiling-point components (B) (predominantly containing ethanol, water, and other low-boiling-point substances), and to yield a bottom solution (C) (predominantly containing butanol and containing small amounts of other high-boiling-point substances).

Conventionally, the bottom solution (C) is subjected to distillation and purification without any treatments, to thereby yield by-produced butanol as a final product. However, the quality of the thus-obtained butanol is unsatisfactory in terms of the results of a chameleon test or sulfuric acid coloring test.

In the sixth invention group, after the bottom solution (C) is subjected to chemical treatment, the resultant solution is subjected to distillation, to thereby separate low-boiling-point components (b) and high-boiling-point components (c), thereby yielding a purified butanol.

Examples of the aforementioned chemical treatment include alkali treatment, reduction treatment, oxidation treatment, and a combination of at least two of these treatments.

(I) Examples of the alkali treatment include treatment making use of an aqueous solution of, for example, lithium hydroxide, sodium hydroxide, or potassium hydroxide, and treatment making use of an alcohol (e.g., ethanol or butanol) solution of such a hydroxide. Alkali treatment by use of a sodium hydroxide aqueous solution is preferred.

When sodium hydroxide treatment is carried out, a 0.5–5% by weight sodium hydroxide aqueous solution is added to the bottom solution (C) such that the content of sodium hydroxide in the solution is 1–2% by weight, and the resultant solution is heated at 90–130° C. for 0.5–10 hours.

(II) Examples of the reduction treatment include a treatment making use of an aqueous solution or alcohol solution of a reducing agent such as sodium borohydride, lithium borohydride, or lithium aluminum hydride; and a treatment making use of an aqueous solution of acetic acid-iron or an alcohol solution of sodium hydroxide-zinc. Reduction treatment using a sodium borohydride aqueous solution is preferred.

When sodium borohydride treatment is carried out, a 0.1–2% by weight sodium borohydride aqueous solution is added to the bottom solution (C) such that the content of sodium borohydride in the solution is 0.5–1%, and the resultant solution is heated at 90–130° C. for 0.5–10 hours, preferably 0.5–2 hours.

(III) Examples of the oxidation treatment include an ozone treatment.

When the ozone treatment is carried out, 0.01–10% by volume ozone is generated in air or oxygen by use of an ozone generating apparatus, and the resultant ozone-containing gas is fed to the bottom solution (C), to thereby subject impurities, which cause lowering of the quality of butanol, to ozone oxidation at room temperature.

The solution which has undergone chemical treatment is further subjected to distillation, to thereby separate the low-boiling-point components (b) and the high-boiling-point components (c), thereby yielding a purified butanol (a).

No particular limitation is imposed on the order of separation of the low-boiling-point components (b) and the high-boiling-point components (c). For example, it may be the case that the low-boiling-point components (b) are distilled off first, and subsequently the purified butanol (a) is distilled out and separated from the high-boiling-point components (c). Alternatively, it may be the case that butanol is separated from the high-boiling-point components (c), and subsequently the low-boiling-point components (b) are distilled off from the butanol, to thereby yield the purified butanol (a) as a bottom product.

Distillation may be carried out by means of a batch-type process or a continuous process.

In the case of continuous distillation, for example, the low-boiling-point components (b) are distilled off, and then butanol is distilled and separated from the high-boiling-point components (c).

The low-boiling-point components (b) are distilled off by distillation under the following conditions. Pressure: reduced or ambient pressure, reflux ratio: 1–10, cut percentage of low-boiling-point components: 5–20% by weight with respect to a fed solution.

The purified butanol (a) is obtained as a distillate and separated from the high-boiling-point components (c) under the following conditions. Pressure: reduced or ambient pressure, reflux ratio: 0.2–3, cut percentage of high-boiling-point components: 5–20% by weight with respect to a fed solution.

When the amount of the bottom solution (C) is not overly large, the solution is stored in a storage tank, and when the amount of the stored solution reaches a predetermined level, the solution is subjected to chemical treatment and batch distillation.

In the case of batch-type distillation, a distillation tower including about 40 actual plates is used, and the low-boiling-point components (b) are distilled under the following conditions: tower top pressure: 300–760 torr, reflux ratio: 2–5, bottom solution temperature: 80–130° C., and then the purified butanol (a) is distilled at the same tower top pressure and reflux ratio and at a bottom solution temperature of 90–150° C.

Purified butanol as a by-product produced through the process of the sixth invention group exhibits a chameleon test measurement value of 15–25 minutes; therefore, it is clear that the quality of the inventive butanol is greatly improved as compared with butanol produced through a conventional process, which typically exhibits a chameleon test measurement value of zero minutes.

The specification to be met by butanol as a product is APHA of 50 or less as measured by a sulfuric acid coloring test. Purified butanol as a by-product obtained by the sixth invention group exhibits APHA of 30–35; therefore, it is clear that the quality of the inventive butanol is improved as compared with butanol produced through a conventional process, which exhibits APHA of 100–200.

Production of Butyl Acetate

Through a known method, the above-obtained purified butanol (a) is reacted with acetic acids, to thereby produce butyl acetate. Examples of the acetic acids include acetic acid, acetic anhydride, and acetic acid chloride, and acetic acid is preferably used.

For example, the purified butanol (a) is reacted with acetic acid in the presence or absence of a catalyst to thereby yield a crude butyl acetate, and then distillation of the crude butyl acetate is carried out, to thereby produce a purified butyl acetate. Examples of the catalyst include sulfuric acid and heteropoly-acid, etc.

The esterification temperature is 70–150° C., preferably 90–130° C. The reaction time is 0.5–5 hours, preferably 1.5–3 hours.

Butyl acetate as a product produced through the process of the sixth invention group exhibits APHA of 20–30 as measured by a sulfuric acid coloring test; therefore, it is clear that the quality of the butyl acetate is improved as compared with butyl acetate produced through a conventional process, which exhibits APHA of 70–90.

EXAMPLES

Examples for the First Invention Group

The inventions of the first invention group will be next described in more detail by way of Examples, which should not be construed as limiting the inventions thereto. It is to be noted that unless otherwise specified, the term "part(s)" used in the Examples refers to "part(s) by weight." The below-described evaluation methods were employed.

1. Potassium permanganate color-fading time (may be referred to as "chameleon test measurement value"): the time is measured according to JIS K1351 3.10 (unit: minute)

2. Odor evaluation rating: rating "1" is assigned to 1,3-butylene glycol which issues no odor, rating "5" is assigned to 1,3-butylene glycol which issues minimal odor, rating "10" is assigned to 1,3-butylene glycol which issues a slight odor, and rating of an evaluation sample (i.e., 1,3-butylene glycol) is determined on the basis of the results of relative evaluation. Odor evaluation was performed as follows. An evaluation sample is mixed with water at a ratio of 1:1, the resultant mixture is placed in a ground stopper reagent bottle, the bottle is sealed and allowed to stand at room temperature, and then the sample is smelled promptly in air and relative comparison of the odor is performed.

3. Time-course deterioration test: a sample is placed in a ground stopper bottle, the vapor phase portion in the bottle is subjected to nitrogen sealing, and then the bottle is sealed. After the bottle is placed in a thermostatic chamber at 40° C. for three months, the sample in the bottle is subjected to measurement of potassium permanganate color-fading time and odor evaluation.

Examples 1-1 and 1-2

The process of the first invention group will be described by way of Examples and with reference to the flowsheet shown in FIG. 1. Acetaldol (100 parts) and hydrogen (6.5 parts) serving as raw materials were placed in a reactor (not illustrated in the FIG. 1) The reactor was maintained at a temperature of 125–135° C. and a pressure of 150 Kg/cm². A Raney nickel (3.5 parts) serving as a catalyst was added to the reactor. A crude reaction mixture was removed from the reactor, the catalyst was separated from the mixture, and the resultant mixture was neutralized with sodium hydroxide. Subsequently, alcohols were removed from the neutralized mixture, and the resultant crude 1,3-butylene glycol was fed into a dehydration tower 1-1 shown in FIG. 1. Through the top of the dehydration tower, water (15 parts) was added with respect to the fed solution (100 parts), dehydration was carried out at a pressure of 50 torr, and a crude 1,3-butylene glycol containing water in an amount of 0.5% by weight or less was obtained from the bottom of the distillation tower. The thus-dehydrated crude 1,3-butylene glycol was then fed into a salt-removal tower 1-2. Salts, high-boiling-point substances, and a portion of 1,3-butylene glycol (total 5 parts on the basis of 100 parts of the fed solution) were discharged, as a residue, from the bottom of the salt-removal tower. From the top of the salt-removal tower, 1,3-butylene glycol, low-boiling-point substances, and a portion of high-boiling-point substances (total 95 parts) were distilled.

The 1,3-butylene glycol, low-boiling-point substances, and high-boiling-point substances distilled from the salt-removal tower 1-2 were fed into a distillation tower 1-3 for removal of high-boiling-point substances, and the high-boiling-point substances and a portion of 1,3-butylene glycol (total 20 parts) were discharged from the bottom of the distillation tower. 1,3-Butylene glycol and low-boiling-point substances (total 80 parts) were distilled off from the top of the distillation tower, and then fed into an alkali reactor 1-4. A 10% by weight sodium hydroxide aqueous solution was added to the fed solution such that the concentration of sodium hydroxide in the solution was 0.2% by weight. In the alkali reactor, reaction was carried out at a reaction temperature of 120° C. for a residence time of 20 minutes (Example 1-1). In Example 1-2, the procedure of Example 1-1 was repeated, except that, in the alkali reactor, the reaction temperature and the residence time were changed to 100° C. and 30 minutes, respectively. A crude reaction mixture obtained from the alkali reactor was fed into an alkali-removal tower 1-5. Alkali, high-boiling-point substances, and a portion of 1,3-butylene glycol (total 10 parts on the basis of 100 parts of the fed solution) were discharged from the bottom of the alkali-removal tower. 1,3-Butylene glycol and low-boiling-point substances (total 90 parts) were distilled from the top of the alkali-removal tower, and then fed into the subsequent final product distillation tower. Low-boiling-point substances and a portion of 1,3-butylene glycol (total 10% by weight on the basis of 100 parts of the fed solution) were obtained as a distillate from the top of the final product distillation tower 1-6. From the bottom of the distillation tower, 1,3-butylene glycol was obtained as a product.

The 1,3-butylene glycol was subjected to measurement of potassium permanganate color-fading time and odor evaluation immediately after production and at a period of three months after production. The results are shown in Table 1-1.

Comparative Example 1-1

The procedure of Example 1-1 was repeated until the step in which the 1,3-butylene glycol, low-boiling-point substances, and high-boiling-point substances obtained as a distillate from the salt-removal tower 1-2 were fed into the distillation tower 1-3 for removal of high-boiling-point substances. Subsequently, 1,3-butylene glycol and low-boiling-point substances were obtained as a distillate from the top of the distillation tower 1-3, and the resultant distillate was fed into the final product distillation tower. Low-boiling-point substances and a portion of 1,3-butylene glycol (total 10% by weight on the basis of 100 parts of the fed solution) were obtained as a distillate from the top of the final product distillation tower 1-6. From the bottom of the distillation tower, 1,3-butylene glycol was obtained as a final product.

Immediately after production, the odor evaluation rating of the 1,3-butylene glycol was 3, and the potassium permanganate color-fading time of the 1,3-butylene glycol was 15 minutes. The 1,3-butylene glycol was subjected to time-course deterioration test at 40° C. At a period of three months after production, the potassium permanganate color-fading time decreased to 3 minutes, the odor evaluation rating was 10, and the 1,3-butylene glycol issued a slight odor. The results are shown in Table 1-1.

TABLE 1-1

|  | Potassium permanganate color-fading time (minutes) | | Odor evaluation rating | |
| --- | --- | --- | --- | --- |
|  | Immediately after production | Three months after production | Immediately after production | Three months after production |
| Example 1-1 | 25 | 10 | 3 | 3 |
| Example 1-2 | 20 | 5 | 3 | 3 |
| Comparative Example 1-1 | 15 | 3 | 3 | 10 |

Examples for the Second Invention Group

The inventions of the second invention group will next be described in more detail by way of Examples, which should not be construed as limiting the inventions thereto.

Odor evaluation method: 1,3-butylene glycol immediately after production or 1,3-butylen glycol which has been stored for a predetermined period of time is used as an evaluation sample; and rating "1" is assigned to 1,3-butylene glycol which issues no odor, rating "5" is assigned to 1,3-butylene glycol which issues minimal odor, rating "10" is assigned to 1,3-butylene glycol which issues a slight odor, and rating (1 to 10) of an evaluation sample is determined on the basis of the results of relative evaluation.

Odor evaluation was performed as follows. 1,3-Butylene glycol is mixed with water at a volume ratio of 1:1, the resultant mixture is placed in a ground stopper reagent bottle, the bottle is sealed and allowed to stand at room temperature, and then the sample is smelled promptly in air and relative comparison of the odor is performed. When the aforementioned rating of 1,3-butylene glycol is 10 or more, the 1,3-butylene glycol is not passed in terms of odor.

Example 2-1

A para-acetaldol reaction mixture was obtained through condensation of acetaldehyde in the presence of a sodium hydroxide aqueous solution, and neutralization of the reaction mixture was carried out. A portion of unreacted acetaldehyde was recovered from the neutralized mixture, and the resultant crude reaction mixture was fed into a continuous suspension bubble tower in which a Raney nickel having the below-described properties was suspended in the mixture. Subsequently, hydrogenation was carried out under the below-described conditions, the Raney nickel was removed through filtration, and a hydrogenation crude mixture was obtained.

The Raney nickel contains nickel in an amount of 49% by weight during alloying, and it showed a grain size distribution of (grains having a size of more than 74 $\mu$m (3.3%), grains having a size of 43 $\mu$m to 74 $\mu$m (17.4%), and grains having a size of 43 $\mu$m or less (79.2%)). After development, the Raney nickel contains aluminum in an amount of 8% by weight, and exhibits an acetone hydrogenation activity of 2,500 ml/g-Ni/hr and a phenol hydrogenation activity of 600 ml/g-Ni/hr.

The catalyst (10 parts by weight) and hydrogen (6 parts by weight) were added to acetaldols (100 parts by weight), and hydrogenation was carried out under the following conditions: residence time: 80 minutes, reaction temperature: 135° C., reaction pressure: 140 atm.

The hydrogenation crude mixture (5 ml) was sampled in a test tube, and a BPB-added hydroxylamine hydrochloride solution (5 ml)—which had been prepared in advance—was added to the crude mixture, and then mixed The time required for changing the color of the test solution from blue to yellow was 16 hours.

The hydrogenation crude mixture was subjected to alcohol-removal treatment, to thereby remove ethanol and butanol. Through azeotropic distillation with water, components causing odor were separated from the resultant crude mixture, and the resultant mixture was subjected to thin-film evaporation, to thereby remove substances neutralized with the base during the condensation step, the hydrogenation catalyst, and thermally decomposable high-boiling-point substances. Subsequently, the resultant solution was fed into a continuous distillation tower including 20 plates, and distillation was carried out under the following conditions: bottom solution temperature: 150° C., tower top pressure: 20 torr, to thereby yield 1,3-butylene glycol as a distillate while high-boiling-point substances (15% by weight on the basis of the fed solution (100% by weight)) were allowed to remain in the distillation tower. The distilled 1,3-butylene glycol was fed into a continuous distillation tower including a packed bed corresponding to 20 plates, and then distillation was carried out under the following conditions: bottom solution temperature: 115° C., tower top pressure: 15 torr, and reflux ratio: 1.5, to thereby remove low-boiling-point substances (15% by weight on the basis of the fed solution (100% by weight)), thereby yielding a purified 1,3-butylene glycol. The odor evaluation rating of the purified 1,3-butylene glycol was 1 immediately after production, and was 5 after storage for three months; i.e., the 1,3-butylene glycol can be used as a material for cosmetics.

Example 2-2

The procedure of Example 2-1 was repeated, except that the following Raney nickel was used, to thereby obtain 1,3-butylene glycol. The Raney nickel contains nickel in an amount of about 51% by weight during alloying, contains aluminum in an amount of 7% by weight after development, and exhibits an acetone hydrogenation activity of 4,300 ml/g-Ni/hr and a phenol hydrogenation activity of 1,200 ml/g-Ni/hr.

It is to be noted that the hydrogenation crude mixture (5 ml) was sampled in a test tube, and a BPB-added hydroxylamine hydrochloride solution (5 ml)—which had been prepared in advance—was added to the crude mixture, and then mixed. The time required for changing the color of the test solution from blue to yellow was 48 hours. The odor evaluation rating of the above-obtained purified 1,3-butylene glycol was 1 immediately after production, and was 3 after storage for three months; i.e., the 1,3-butylene glycol can be used as a material for cosmetics.

Comparative Example 2-1

The procedure of Example 2-1 was repeated, except that the following Raney nickel was used, to thereby obtain 1,3-butylene glycol. The Raney nickel contains nickel in an amount of about 50% by weight during alloying, contains aluminum in an amount of 7% by weight after development, and exhibits an acetone hydrogenation activity of 1,500 ml/g-Ni/hr and a phenol hydrogenation activity of 350 ml/g-Ni/hr.

It is to be noted that the hydrogenation crude mixture (5 ml) was sampled in a test tube, and a BPB-added hydroxylamine hydrochloride solution (5 ml)—which had been prepared in advance—was added to the crude mixture, and then mixed. The discoloration time of the test solution was 0.8 hour. The odor evaluation rating of the above-obtained purified 1,3-butylene glycol was 5 immediately after production, and was 10 after storage for three months.

Examples for the Third Invention Group

The inventions of the third invention group will next be described in more detail by way of Examples, which should not be construed as limiting the inventions thereto.

Example 3-1

An acetaldehyde aqueous solution (acetaldehyde/water= 90/10 by weight) (500 parts by weight), which had been prepared in advance, was placed in a 1-liter aldol condensation reactor equipped with a jacket, and then cooled to 15–20° C. Subsequently, a 0.5% sodium hydroxide aqueous solution (10 parts by weight) was gradually added dropwise to the acetaldehyde aqueous solution while the solution was stirred vigorously, and then the resultant mixture was allowed to react at a reaction temperature of 20° C. for seven hours. Subsequently, the resultant reaction mixture was neutralized with a 10% by volume diluted acetic acid aqueous solution in a neutralization bath, and the resultant mixture was subjected to aging for two hours. Then, the resultant mixture was continuously fed to an aldoxane decomposition tower, and thermal decomposition was carried out.

A distillate containing acetaldehyde, crotonaldehyde, and water was discharged from the top of the aldoxane decomposition tower, and a bottom solution containing acetaldols including aldoxane and paraldols as a primary component, remaining crotonaldehyde and other substances as a secondary component, and water was continuously discharged from the bottom of the tower. In an intermediate bath, the acidity of the bottom solution was adjusted to 2 by use of the aforementioned diluted acetic acid solution, and the resultant solution was used as a raw material for hydrogenation.

The thus-obtained raw material for hydrogenation was continuously fed to a continuous suspension bubble tower (made from carbon steel) in which a Raney nickel serving as a hydrogenation catalyst was suspended in the raw material, and hydrogenation was carried out under the below-described reaction conditions. Subsequently, the Raney nickel was removed through filtration, and a hydrogenation crude mixture was obtained.

The catalyst (10 parts by weight) and hydrogen (6 parts by weight) were added to acetaldols (100 parts by weight) in the raw material for hydrogenation, and hydrogenation was carried out under the following conditions: residence time: 80 minutes, reaction temperature: 135° C., reaction pressure: 140 atm. After the hydrogenation was continuously carried out for 24 hours, the yield of 1,3-butylene glycol in the hydrogenation crude mixture was 85% by weight, and the by-production percentage of butanol was 1.8% by weight.

Example 3-2

The procedure of Example 3-1 was repeated, except that the acidity of the bottom solution was adjusted to 10 by use of a 10% by volume diluted acetic acid solution in an intermediate bath, and the resultant solution was used as a raw material for hydrogenation.

After hydrogenation reaction was continuously carried out for 24 consecutive hours, the yield of 1,3-butylene glycol in a hydrogenation crude mixture was 84% by weight. After production of 1,3-butylene glycol was carried out for 2,000 hours, the hydrogenation reactor was observed and no corrosion was found.

Comparative Example 3-1

The procedure of Example 3-1 was repeated, except that the bottom solution was not acidified in an intermediate bath, and was used as a raw material for hydrogenation without any treatments.

After hydrogenation reaction was continuously carried out for 24 hours, the yield of 1,3-butylene glycol in a hydrogenation crude mixture was 50% by weight. The used hydrogenation catalyst was removed from the hydrogenation reactor, washed with water, dried, and then subjected to analysis. The analysis results reveal that polycondensation of the raw material for hydrogenation proceeded in the Raney nickel catalyst, and the properties of the catalyst were lowered.

Comparative Example 3-2

The procedure of Example 3-1 was repeated, except that the acidity of the bottom solution was adjusted so as to fall within a range of 95 to 105 by use of acetic acid in an intermediate bath, and the resultant solution was used as a raw material for hydrogenation.

After hydrogenation reaction was continuously carried out for 24 hours, the yield of 1,3-butylene glycol in a hydrogenation crude mixture was 80% by weight, and the by-production percentage of butanol was increased to 3.0% by weight.

Examples for the Fourth Invention Group

The inventions of the fourth invention group will next be described in more detail by way of Examples, which should not be construed as limiting the inventions thereto.

Odor evaluation method: rating "1" is assigned to 1,3-butylene glycol which issues no odor, rating "5" is assigned to 1,3-butylene glycol which issues minimal odor, rating "10" is assigned to 1,3-butylene glycol which issues a slight odor, and rating of an evaluation sample (i.e., 1,3-butylene glycol) is determined on the basis of the results of relative evaluation.

Odor evaluation was performed as follows. 1,3-Butylene glycol is mixed with water at a volume ratio of 1:1, the resultant mixture is placed in a ground stopper reagent bottle, the bottle is sealed and allowed to stand at room temperature, and then the sample is smelled promptly in air and relative comparison of the odor is performed. When the aforementioned rating of 1,3-butylene glycol is 10 or more, the 1,3-butylene glycol is not passed in terms of odor.

Example 4-1

An acetaldehyde aqueous solution (acetaldehyde/water= 90/10 by weight) (500 parts by weight), which had been prepared in advance, was placed in a 1-liter aldol condensation reactor equipped with a jacket, and then cooled to 15–20° C. Subsequently, a 0.5% sodium hydroxide aqueous solution (10 parts by weight) was gradually added dropwise to the acetaldehyde aqueous solution while the solution was stirred vigorously, and then the resultant mixture was allowed to react while maintaining a reaction temperature at 20° C. for seven hours. Subsequently, the resultant reaction mixture was neutralized with a 10% by volume diluted acetic acid aqueous solution in a neutralization bath, and the resultant mixture was subjected to aging for two hours. Then, the resultant mixture was continuously fed to an aldoxane decomposition tower, and thermal decomposition was carried out.

A distillate containing acetaldehyde, crotonaldehyde, and water was discharged from the top of the aldoxane decomposition tower, and a bottom solution containing para-acetaldols including aldoxane and paraldol as a primary component, remaining crotonaldehyde and other substances as a secondary component, and water was continuously discharged from the bottom of the tower. In an intermediate bath, the acidity of the bottom solution was adjusted to 10 by use of the aforementioned diluted acetic acid solution, and the resultant solution was used as a raw material for hydrogenation.

Here, acidity refers to an amount (ml) of a 1/10 N sodium hydroxide aqueous solution to be required for neutralizing 100 ml of a sample (indicator: phenolphthalein).

The thus-obtained raw material for hydrogenation was continuously fed to a continuous suspension bubble tower in which a Raney nickel serving as a hydrogenation catalyst was suspended in the raw material, and hydrogenation was carried out under the below-described reaction conditions. Subsequently, the Raney nickel was removed through filtration, and a hydrogenation crude mixture was obtained.

The catalyst (10 parts by weight) and hydrogen (6 parts by weight) were added to acetaldols (100 parts by weight) in the raw material for hydrogenation, and hydrogenation was carried out under the following conditions: residence time: 80 minutes, reaction temperature: 135° C., reaction pressure: 140 atm. Immediately after the hydrogenation, the hydrogenation crude mixture contained ethanol (8% by weight), butanol (1.6% by weight), and 1,3-butylene glycol (85% by weight).

A 10% by weight sodium hydroxide aqueous solution was added to the hydrogenation crude mixture immediately after hydrogenation, and the pH of the crude mixture was adjusted to 11. Subsequently, ethanol and butanol were distilled off from the crude mixture, the resultant mixture was subjected to dehydration distillation, and then neutralized salts, sodium hydroxide, the catalyst, and thermally decomposable high-boiling-point substances were separated from the resultant mixture by use of a thin-film evaporator. Thereafter, the resultant solution was fed to a continuous distillation tower including 20 plates, and then distillation was carried out under the following conditions: bottom solution temperature: 150° C., and tower top pressure: 20 torr, to thereby remove high-boiling-point substances (15% by weight on the basis of the fed solution (100% by weight)) from the bottom of the tower, thereby yielding 1,3-butylene glycol distillate having a purity of 99.2% by weight. The recovery percentage of 1,3-butylene glycol from the hydrogenation crude mixture was 90% by weight. Coloring of the 1,3-butylene glycol distillate was not observed, and the odor evaluation rating of the 1,3-butylene glycol distillate was 5.

Example 4-2

The procedure of Example 4-1 was repeated, except that the pH of the hydrogen crude mixture immediately after hydrogenation was adjusted to 11.5. The recovery percentage of 1,3-butylene glycol from the hydrogenation crude mixture was 88% by weight. Discoloration of 1,3-butylene glycol distillate was not observed, and the odor evaluation rating of the 1,3-butylene glycol distillate was 3.

Comparative Example 4-1

An acidic hydrogenation crude mixture immediately after hydrogenation, which mixture was obtained through the procedure of Example 4-1, was subjected to alcohol removal treatment in a manner similar to that of Example 4-1, to thereby remove ethanol, butanol, acetic acid, etc. Subsequently, neutralized salts, the catalyst, and thermally decomposable high-boiling-point substances were removed from the resultant mixture by use of a thin-film evaporator. Thereafter, the resultant solution was fed to a continuous distillation tower including 20 plates, and then distillation was carried out under the following conditions: bottom solution temperature: 150° C., and tower top pressure: 20 torr, to thereby remove high-boiling-point substances (20% by weight on the basis of the fed solution (100% by weight)) from the bottom of the tower, thereby yielding 1,3-butylene glycol distillate having a purity of 98% by weight.

The recovery percentage of 1,3-butylene glycol from the hydrogenation crude mixture was 83% by weight. The purity and yield of the thus-obtained 1,3-butylene glycol were low as compared with those of 1,3-butylene glycol obtained in Example 4-1.

Comparative Example 4-2

The procedure of Example 4-1 was repeated, except that the pH of the hydrogen crude mixture immediately after hydrogenation was adjusted to 13. The odor evaluation rating of the thus-obtained 1,3-butylene glycol was about 15, and discoloration of the 1,3-butylene glycol was observed; i.e., the quality of the 1,3-butylene glycol was low as compared with that of 1,3-butylene glycol obtained in Example 4-1. The 1,3-butylene glycol of Comparative Example 4-2 was not passed as a product.

Examples for the Fifth Invention Group

The inventions of the fifth invention group will next be described in more detail by way of Examples, which should not be construed as limiting the inventions thereto.

Odor evaluation method: rating "1" is assigned to 1,3-butylene glycol which issues no odor, rating "5" is assigned to 1,3-butylene glycol which issues minimal odor, rating "10" is assigned to 1,3-butylene glycol which issues a slight odor, and rating of an evaluation sample (i.e., 1,3-butylene glycol) is determined on the basis of the results of relative evaluation.

Odor evaluation was performed as follows. 1,3-Butylene glycol is mixed with water at a volume ratio of 1:1, the resultant mixture is placed in a ground stopper reagent bottle, the bottle is sealed and allowed to stand at room temperature, and then the sample is smelled promptly in air and relative comparison of the odor is performed. When the aforementioned rating of 1,3-butylene glycol is 10 or more, the 1,3-butylene glycol is not passed in terms of odor.

There was used an experimental ozone generator in which, when air is fed at a rate of 20 NL (normal liter)/hour, ozone (0.28% by volume; i.e., 0.12 g/hour) can be generated through discharge at 60 V, ozone (0.63% by volume; i.e., 0.27 g/hour) can be generated through discharge at 80 V, and ozone (0.96% by volume; i.e., 0.41 g/hour) can be generated through discharge at 100 V.

Example 5-1

A para-acetaldol reaction mixture was obtained through condensation of acetaldehyde in the presence of a sodium hydroxide aqueous solution, and the reaction mixture was subjected to neutralization treatment. Subsequently, unreacted acetaldehyde was separated and removed from the neutralized mixture, and the resultant para-acetaldol solution was fed into a continuous suspension bubble tower in which a Raney nickel serving as a hydrogenation catalyst was suspended in the solution. Subsequently, hydrogenation was carried out under the below-described conditions, the Raney nickel was removed through filtration, and a hydrogenation crude mixture was obtained.

The catalyst (10 parts by weight) and hydrogen (6 parts by weight) were added to para-acetaldol (100 parts by weight), and hydrogenation was carried out under the following reaction conditions: residence time: 80 minutes, reaction temperature: 135° C., reaction pressure: 140 atm.

The hydrogenation crude mixture was subjected to alcohol-removal treatment, to thereby remove ethanol and butanol. The resultant mixture was subjected to flash distillation, to thereby remove neutralized salts, the catalyst, and thermally decomposable high-boiling-point substances. Subsequently, the resultant solution was fed into a continuous distillation tower including 20 plates, and distillation was carried out under the following conditions: bottom solution temperature: 150° C., tower top pressure: 20 torr, to thereby remove high-boiling-point substances (15% by weight on the basis of the fed solution (100% by weight)) from the bottom of the tower, thereby obtaining 1,3-butylene glycol distillate (D1).

The 1,3-butylene glycol distillate (D1) was fed at a rate of 2 kg/hour to the bottom of a vertical reactor (internal diameter: 10 cm, height: 25 cm, capacity: 2 liters) including a stirring apparatus. Air containing 0.28% by volume ozone was blown into the reactor at 20 NL/hour, to thereby subject the 1,3-butylene glycol distillate to an ozone treatment. The amount of ozone fed to the reactor was 0.12 g/hour. The odor evaluation rating of purified 1,3-butylene glycol after the ozone treatment was 5, and the purified 1,3-butylene glycol issued minimal odor. The 1,3-butylene glycol distillate (D1) was subjected merely to the ozone treatment, and thus the yield of the purified 1,3-butylene glycol was high.

Comparative Example 5-1

The odor of the 1,3-butylene glycol distillate (D1) obtained in Example 5-1 was not itself satisfactorily improved. Therefore, the 1,3-butylene glycol distillate (D1) was fed into a continuous distillation tower including a packed bed corresponding to 20 plates, and then distillation was carried out under the following conditions: bottom solution temperature: 115° C., tower top pressure: 15 torr, and reflux ratio: 3, to thereby remove low-boiling-point substances (20% by weight on the basis of the fed solution (100% by weight)), thereby obtaining a purified 1,3-butylene glycol.

Similarly to the case of the purified 1,3-butylene glycol of Example 5-1, the thus-obtained purified 1,3-butylene glycol issued minimal odor. However, since the reflux ratio during removal of low-boiling-point components was high, and the amount of the removed low-boiling-point components was large, the distillation yield of the purified 1,3-butylene glycol of Comparative Example 5-1 was low as compared with that of the purified 1,3-butylene glycol of Example 5-1.

Example 5-2

The ozone-treated 1,3-butylene glycol obtained in Example 5-1 was fed into a continuous distillation tower including a packed bed corresponding to 20 plates, and then distillation was carried out under the following conditions: bottom solution temperature: 115° C., tower top pressure: 15 torr, and reflux ratio: 1.5, to thereby remove low-boiling-point substances (5% by weight on the basis of the fed solution (100% by weight)), thereby obtaining a purified 1,3-butylene glycol.

The odor evaluation rating of the purified 1,3-butylene glycol was 1 immediately after production; i.e., the 1,3-butylene glycol issued no odor. The odor evaluation rating of the 1,3-butylene glycol was 3 after storage for three months, and thus the 1,3-butylene glycol can be beneficially used as a material of cosmetics grade. During distillation, the reflux ratio was low, and the amount of the removed low-boiling-point components was small.

Comparative Example 5-2

The hydrogenation crude mixture obtained in Example 5-1 was subjected to an alcohol-removal treatment, to thereby remove ethanol and butanol. The resultant solution was subjected to flash distillation, to thereby remove the catalyst and thermally decomposable high-boiling-point substances. Subsequently, a 10% by weight sodium hydroxide aqueous solution was added to the resultant solution such that the amount of sodium hydroxide in the solution was 0.5% by weight, and the resultant solution was subjected to distillation. 1,3-Butylene glycol was obtained as a distillate from the top of a distillation tower, and high-boiling-point substances, sodium hydroxide, and a portion of 1,3-butylene glycol were removed from the bottom of the tower. The percentage of the substances removed from the bottom on the basis of the entirety of the fed solution was 15 wt. %.

The distillate 1,3-butylene glycol was fed to a distillation tower, and further subjected to distillation. Low-boiling-point substances and a portion of 1,3-butylene glycol were obtained as a distillate from the top of the tower, and a purified 1,3-butylene glycol was obtained from the bottom of the tower. The cut percentage in bottom of the substances obtained as a distillate from the top on the basis of the entirety of the fed solution was 5% by weight. The odor evaluation rating of the thus-obtained purified 1,3-butylene glycol was 5, which is the same as that of the purified 1,3-butylene glycol of Example 5-1. However, the distillation yield of the 1,3-butylene glycol of Comparative Example 5-2 is low as compared with that of the 1,3-butylene glycol of Example 5-1, since removal of low-boiling-point substances was carried out. The odor of the 1,3-butylene glycol of Comparative Example 5-2 was not satisfactorily improved as compared with that of the 1,3-butylene glycol of Example 5-2 from which low-boiling-point substances were removed.

Examples for the Sixth Invention Group

The inventions of the sixth invention group will next be described in more detail by way of Examples, which should not be construed as limiting the inventions thereto.

Test methods for butanol and butyl acetate are described below.

(1) Chameleon test: the test is carried out according to JIS K1351 3.10. A potassium permanganate solution of predetermined concentration is added to a test sample solution, and the time required for causing the color of the sample solution to fade into the color of a standard solution for comparison—the color of the sample solution being faded due to an easily oxidizable substance—is measured (unit: minutes or hours)

(2) Sulfuric acid coloring test: special-grade reagent sulfuric acid (40 ml) is added dropwise (2 ml/minute) to a test sample solution of 30° C., the resultant mixture is stirred and then allowed to stand for five minutes, and the degree of coloring is measured by comparison of the color of the sample solution with that of a standard APHA solution (unit: APHA)

Example 6-1

A para-acetaldol reaction mixture was obtained through condensation of acetaldehyde in the presence of a sodium hydroxide aqueous solution, and the reaction mixture was subjected to neutralization treatment. Subsequently, unreacted acetaldehyde and a portion of by-produced crotonaldehyde were removed from the thus-neutralized mixture, to thereby obtain a para-acetaldol solution (containing the remaining by-produced crotonaldehyde). A portion of acetaldehyde was recovered from the above-removed unreacted acetaldehyde, and the remaining unreacted acetaldehyde and the above-removed by-produced crotonaldehyde were added to the para-acetaldol solution. Thereafter, the resultant para-acetaldol solution was fed into a continuous suspension bubble tower in which a Raney nickel serving as a hydrogenation catalyst was suspended in the solution. Subsequently, hydrogenation was carried out under the below-described conditions, the Raney nickel was removed through filtration, and a hydrogenation crude mixture was obtained.

The catalyst (10 parts by weight) and hydrogen (6 parts by weight) were added to para-acetaldol (100 parts by weight), and hydrogenation was carried out under the following conditions: residence time: 80 minutes, reaction temperature: 135° C., reaction pressure: 140 atm.

The hydrogenation crude mixture contained 1,3-butylene glycol (60% by weight), ethanol (15% by weight), butanol (10% by weight), water (10% by weight), and other low-boiling-point substances and high-boiling-point substances. The hydrogenation crude mixture was subjected to distillation, to thereby distill, from 1,3-butylene glycol, a distillate (A1) (32 parts by weight) including ethanol, butanol, water, other low-boiling-point substances, and small amounts of high-boiling-point substances. The distillation for removal of alcohols was carried out under the following conditions: pressure: ambient pressure, tower bottom temperature: 120° C., and reflux ratio: 3.

The distillate (A1) was further subjected to distillation, to thereby yield low-boiling-point components (B1) (including ethanol, water, and other low-boiling-point substances) as a distillate, and obtain a bottom solution (C1).

The distillation for removal of the low-boiling-point components was carried out under the following conditions: pressure: ambient pressure, bottom temperature: 130° C., and reflux ratio: 5.

A 5% by weight sodium hydroxide aqueous solution (2 parts by weight) was added to the bottom solution (C1) (100 parts by weight), and the resultant mixture was heated at 105° C. for 1.5 hours.

The thus-heated solution was fed to the bottom of a distillation tower including 40 actual plates, the tower being provided in a batch-type distillation apparatus, and distillation was carried out under the following conditions: tower top pressure: 760 torr, reflux ratio: 3, and bottom solution temperature: 120–130° C., to thereby yield low-boiling-point components as a distillate. Subsequently, a purified butanol was obtained as a distillate from the tower under the following conditions: tower top pressure: 760 torr, reflux ratio: 3, and bottom solution temperature: 130–140° C. The thus-obtained purified butanol exhibited a chameleon test value of 20 minutes, and a sulfuric acid coloring test value (APHA) of 30.

Acetic acid (81 parts by weight) and sulfuric acid (0.3 parts by weight) were added to the purified butanol (100 parts by weight), and the resultant mixture was subjected to esterification reaction at 110° C. for two hours. Subsequently, the catalyst was neutralized with slaked lime, and the resultant reaction mixture was subjected to filtration. The resultant filtrate was subjected to batch distillation under the below-described conditions, to thereby obtain purified butyl acetate.

The purified butyl acetate was obtained as a distillate under the following conditions: the number of plates of distillation tower: 30, tower top pressure: 760 torr, reflux ratio: 5, and bottom solution temperature: 130–140° C. The purified butyl acetate exhibited a sulfuric acid coloring test value (APHA) of 20.

Example 6-2

A 0.5% by weight sodium borohydride aqueous solution (1.0 part by weight) was added to the bottom solution (C1) obtained in Example 6-1 (100 parts by weight), and the resultant mixture was heated at 100° C. for two hours. The thus-heated solution was fed to the bottom of a distillation tower including 40 actual plates, the tower being provided in a batch-type distillation apparatus, and distillation was carried out under the following conditions: tower top pressure: 760 torr, reflux ratio: 3, and bottom solution temperature: 120–130° C., to thereby yield low-boiling-point components as a distillate. Subsequently, purified butanol was obtained as a distillate from the tower under the following conditions: tower top pressure: 760 torr, reflux ratio: 3, and bottom solution temperature: 130–140° C.

The thus-obtained purified butanol exhibited a chameleon test value of 20 minutes, and a sulfuric acid coloring test value (APHA) of 35. In a manner similar to that of Example 6-1, a purified butyl acetate was produced from the purified butanol. The purified butyl acetate exhibited a sulfuric acid coloring test value (APHA) of 25.

Comparative Example 6-1

The bottom solution (C1) obtained in Example 6-1 (100 parts by weight) was directly fed to the bottom of a distillation tower including 40 actual plates without any treatments, the tower being provided in a batch-type distillation apparatus, and distillation was carried out under the following conditions: tower top pressure: 760 torr, reflux ratio: 3, and bottom solution temperature: 120–130° C., to thereby yield low-boiling-point components as a distillate. Subsequently, a purified butanol was obtained as a distillate from the tower under the following conditions: tower top pressure: 760 torr, reflux ratio: 3, and bottom solution temperature: 130–140° C.

The thus-obtained purified butanol exhibited a chameleon test value of 0 minutes, and a sulfuric acid coloring test value (APHA) of 150. In a manner similar to that of Example 6-1, a purified butyl acetate was produced from the purified butanol. The purified butyl acetate exhibited a sulfuric acid coloring test value (APHA) of 90.

INDUSTRIAL APPLICABILITY

According to the first invention group, there is provided 1,3-butylene glycol of high purity, which exhibits potassium permanganate color-fading time of at least five minutes as measured three months after production, and which issues no odor and undergoes minimal change in quality with passage of time.

According to the second invention group, a purified 1,3-butylene glycol can be produced efficiently and reliably, the 1,3-butylene glycol having high purity, not issuing any problematic odor, and not requiring cumbersome production steps including a hydrogenation step and a distillation-purification step. The purified 1,3-butylene glycol can be used as a raw material of synthetic resins, surfactants, hygroscopic agents, high-boiling-point solvents, and anti-freezes. Particularly, the 1,3-butylene glycol can be used as a material for cosmetics, since it has hygroscopicity, low volatility, and low toxicity.

According to the third invention group, there is provided 1,3-butylene glycol which is produced economically and at a high product yield, and which can be used as a raw material of synthetic resins, surfactants, hygroscopic agents, high-boiling-point solvents, and antifreezes. Particularly, the 1,3-butylene glycol can be used as a material for cosmetics, since it has hygroscopicity, low volatility, and low toxicity.

According to the fourth invention group, there is provided 1,3-butylene glycol of high purity which is produced economically and at a high product yield, and which can be used as a raw material of synthetic resins, surfactants, hygroscopic agents, high-boiling-point solvents, and antifreezes. Particularly, the 1,3-butylene glycol can be used as a material for cosmetics, since it has hygroscopicity, low volatility, and low toxicity.

According to the fifth invention group, there can be produced, economically and at high yield, a purified 1,3-butylene glycol which has high purity and does not issue any problematic odor. The purified 1,3-butylene glycol can be used as a raw material of synthetic resins, surfactants, hygroscopic agents, high-boiling-point solvents, and anti-freezes. Particularly, the 1,3-butylene glycol can be used as a material for cosmetics, since it has hygroscopicity, low volatility, and low toxicity.

According to the sixth invention group, there is obtained a purified butanol which exhibits excellent chameleon test value and sulfuric acid coloring test value. In addition, there is provided a purified butyl acetate of high quality which is produced from the butanol.

What is claimed is:

1. A 1,3 butylene glycol which, at a period of three months after production, exhibits potassium permanganate color-fading time of at least five minutes as measured according to JIS K1351 3.10.

2. A 1,3-butylene glycol according to claim 1, which is produced through hydrogenation of acetaldols in the presence of a catalyst.

3. A process for producing a purified 1,3-butylene glycol, which comprises hydrogenating, in the presence of a catalyst, acetaldols obtained through condensation of acetaldehyde, to thereby yield a hydrogenation crude mixture containing 1,3-butylene glycol, wherein the catalyst is Raney nickel having an acetone hydrogenation activity of 2,000 ml/g-Ni/hr or more and/or a phenol hydrogenation activity of 500 ml/g-Ni/hr or more.

4. A process for producing a purified 1,3-butylene glycol according to claim 3, wherein the content of the aldehyde groups remaining in the hydrogenation crude mixture is 200 ppm by weight or less.

5. A process for producing a purified 1,3-butylene glycol according to claim 3 wherein the hydrogenation crude mixture is subjected to distillation to thereby separate low-boiling-point components (L), and then the resultant mixture is further subjected to distillation to thereby yield 1,3-butylene glycol as a distillate.

6. A process for producing a purified 1,3-butylene glycol according to claim 4, wherein the hydrogenation crude mixture is subjected to distillation to thereby separate low-boiling-point components (L), and then the resultant mixture is further subjected to distillation to thereby yield 1,3-butylene glycol-butylene glycol as a distillate.

7. A process for producing a purified 1,3-butylene glycol according to claim 5, wherein, after the low-boiling-point components (L) are separated, the resultant mixture is subjected to evaporation treatment, and then the resultant mixture is further subjected to distillation to thereby yield 1,3-butylene glycol as a distillate.

8. A process for producing a purified 1,3-butylene glycol according to claim 6, wherein, after the low-boiling-point components (L) are separated, the resultant mixture is subjected to evaporation treatment, and then the resultant mixture is further subjected to distillation to thereby yield 1,3-butylene glycol as a distillate.

9. A process for producing a purified 1,3-butylene glycol according to any one of claims 5 through 8, wherein the hydrogenation crude mixture is subjected to distillation to thereby yield 1,3-butylene glycol as a distillate, and the 1,3-butylene glycol is subjected to distillation to thereby separate low-boiling-point components (1).

10. A process for producing a purified 1,3-butylene glycol according to any of claims 3 through 8, wherein, after the low-boiling-point components (L) are separated, the resultant mixture is subjected to evaporation treatment, and then the resultant mixture is further subjected to distillation to thereby yield 1,3-butylene glycol as a distillate.

11. A process for producing a purified 1,3-butylene glycol according to claim 9, wherein, after the low-boiling-point components (L) are separated, the resultant mixture is subjected to evaporation treatment, and then the resultant mixture is further subjected to distillation to thereby yield 1,3-butylene glycol as a distillate.

12. A process for producing a purified 1,3-butylene glycol according to claim 10, wherein the odor of 1,3-butylene glycol as evaluated after storage for three months has a rating of 5 or less.

13. A process for producing a purified 1,3-butylene glycol according to claim 11, wherein the odor of 1,3-butylene glycol as evaluated after storage for three months has a rating of 5 or less.

14. A process for purifying 1,3-butylene glycol, which comprises hydrogenating, in the presence of a catalyst, acetaldols obtained through condensation of acetaldehyde, to thereby synthesize 1,3-butylene glycol; and subjecting the 1,3-butylene glycol to distillation, wherein a hydrogenation crude mixture is basified, alcohols are removed from the mixture, and then a resultant mixture is subjected to distillation.

15. A process for purifying 1,3-butylene glycol according to claim 14, wherein alcohols are removed from the hydrogenation crude mixture, and the mixture is subjected to evaporation treatment, and then the resultant mixture is subjected to distillation.

16. A process for purifying 1,3-butylene glycol according to claim 14, wherein the basified hydrogenation crude mixture has a pH of 9–12.

17. A process for purifying 1,3-butylene glycol according to claim 15, wherein the basified hydrogenation crude mixture has a pH of 9–12.

18. A process for purifying 1,3-butylene glycol according to any one of claims 15, through 17, wherein the hydrogenation crude mixture is basified by use of sodium hydroxide or potassium hydroxide.

19. A process for purifying 1,3-butylene glycol according to any one of claims 15 through 17, wherein the hydrogenation crude mixture is basified after hydrogenation is carried out under a neutral or acidic condition.

20. A process for purifying 1,3-butylene glycol according to claim 18, wherein the hydrogenation crude mixture is basified after hydrogenation is carried out under a neutral or acidic condition.

21. A process for producing a purified 1,3-butylene glycol, which comprises hydrogenating, in the presence of a catalyst, acetaldols obtained through condensation of acetaldehyde, to thereby synthesize 1,3-butylene glycol; and subjecting the 1,3-butylene glycol to distillation, wherein, after a hydrogenation crude mixture is subjected to distillation to thereby separate low-boiling-point components (L), 1,3-butylene glycol is obtained as a distillate from the mixture, and the 1,3butylene glycol distillate (D) is treated with ozone.

22. A process for producing a purified 1,3-butylene glycol according claim 21, wherein, after the hydrogenation crude mixture is subjected to distillation to thereby separate the low-boiling-point components (L), the mixture is promptly subjected to evaporation treatment, followed by distillation to thereby obtain the 1,3-butylene glycol distillate (D).

23. A process for producing a purified 1,3-butylene glycol according to claim 21, wherein the ozone treatment is carried out by bringing 1 kg of the 1,3-butylene glycol distillate (D) into contact with 0.001–1 g of ozone.

24. A process for producing a purified 1,3-butylene glycol according to claim 22, wherein the ozone treatment is carried out by bringing 1 kg of the 1,3-butylene glycol distillate (D) into contact with 0.001–1 g of ozone.

25. A process for producing a purified 1,3-butylene glycol according to any one of claims 21 through 24, wherein low-boiling-point components (1) are separated from the ozone-treated 1,3-butylene glycol.

26. A process for producing a purified 1,3 butylene glycol according to any one of claims 3 to 8, wherein the odor of 1,3-butylene glycol as evaluated immediately after production has a rating of 3 or less.

27. A process for producing a purified 1,3 butylene glycol according to claim 9 wherein the odor of 1,3-butylene glycol as evaluated immediately after production has a rating of 3 or less.

28. A process for producing a purified 1,3 butylene glycol according to claim 10 wherein the odor of 1,3-butylene glycol as evaluated immediately after production has a rating of 3 or less.

* * * * *